United States Patent [19]

Ogawa et al.

[11] Patent Number: 5,500,533

[45] Date of Patent: Mar. 19, 1996

[54] METHOD AND APPARATUS FOR MEASURING ULTRAVIOLET PROTECTION EFFECTIVENESS

[75] Inventors: Katsuki Ogawa; Shigenori Kumagai; Harumi Odagiri, all of Yokohama, Japan

[73] Assignee: Shiseido Company, Ltd., Tokyo, Japan

[21] Appl. No.: 313,460

[22] Filed: Sep. 27, 1994

[30] Foreign Application Priority Data

Sep. 27, 1993 [JP] Japan .................... 5-239875

[51] Int. Cl.$^6$ .................. G01N 21/33
[52] U.S. Cl. .................... 250/372
[58] Field of Search ............ 250/372 R, 372 EM

[56] References Cited

U.S. PATENT DOCUMENTS 5,148,023  9/1992  Hayashi et al. ............. 250/372 EM

OTHER PUBLICATIONS

Cumpelik, "Subscreens At Skin Application Levels: Direct Spectrophotometric Evaluation", *J. Soc. Cosmet. Chem.*, vol. 31:361–366, (1980).

Sayre et al., "Sunscreen Testing Methods: In Vitro Predictions of Effectiveness", *J. Soc. Cosmet. Chem.*, vol. 31:133–143, (1980).

Petro, "Correlation of Spectrophotometric Data With Sunscreen Protection Factors", *International Journal of Cosmetic Science*, vol. 3:185–196, (1981).

Diffey et al., "A New Substrate To Measure Sunscreen Protection Factors Throughout The Ultraviolet Spectrum", *J. Soc. Cosmet. Chem.*, vol. 40:127–133, (1989).

Willis et al., "Effects Of Long Ultraviolet Rays On Human Skin: Photoprotective Or Photoaugmentative", *The Journal Of Investigative Dermatology*, vol. 59, No. 6, pp. 416–420, (1973).

Kaidbey et al., "Further Studies Of Photoaugmentation In Humans: Phototoxic Reactions", *The Journal Of Investigative Dermatology*, vol. 65:472–475, (1975).

Primary Examiner—Carolyn E. Fields
Attorney, Agent, or Firm—Foley & Lardner

[57] ABSTRACT

Provisions are made so that an SPF value having high correlation with an in vivo SPF value can be calculated in vitro using a common calculation equation regardless of the material type used. Transmitted UV intensities $I(\lambda)$ are corrected by respective erythemal effectiveness coefficients $EE(\lambda)$ to calculate an erythema-inducing UV intensity EUI, and the elements of $I(\lambda)$ from $\lambda=320$ to $400$ nm are summed to calculate a transmitted UV-A intensity; then, from the ratio UV-A/EUI, a theoretical value $\alpha_{TH}$ is calculated for the base $\alpha$ of a photoaugmentative effectiveness $\alpha^{UVA}$, and using $EUI \times \alpha_{TH}^{UVA}$, an ultimate theoretical value $EUI_{UL}$ of EUI is calculated. When $EUI_{UL}$ is larger than 75, the SPF value is calculated from $1350/EUI_{UL}$; otherwise, the SPF value is calculated using an empirical equation.

15 Claims, 25 Drawing Sheets

Fig.17

| SAMPLE NO. | ACTIVE INGREDIENT (%) | | | | in vivo SPF (MEAN ± STANDARD DEVIATION) | EUI (ΣEE(I)I(I)) | UVA (mW/cm²) |
|---|---|---|---|---|---|---|---|
| | Parsol MCX *1 | ASL-24 *2 | ULTRA-FINE TiO2 (0.03-0.05 μm) | NORMAL TiO2 (0.3-0.8 μm) | | | |
| A | 5 | — | — | — | 3.9 ± 1.1 | 44.51 | 12.08 |
| B | 4 | — | — | — | 4.1 ± 0.8 | 54.35 | 12.02 |
| C | 2 | — | — | 5 | 5.9 ± 1.2 | 95.80 | 5.31 |
| D | 7.5 | — | 0.5 | — | 14.3 ± 2.8 | 21.35 | 9.56 |
| E | 7.5 | — | 0.5 | — | 15.0 ± 2.0 | 27.93 | 9.30 |
| F | — | — | 10 | 12.5 | 18.2 ± 0.9 | 62.38 | 1.61 |
| G | — | — | 16 | 10 | 20.3 ± 4.3 | 45.44 | 1.34 |
| H | — | — | 20 | 10 | 26.9 ± 8.4 | 19.22 | 0.61 |
| I | 7.5 | 2 | 7.5 | — | 28.7 ± 3.0 | 8.45 | 3.98 |
| J | — | — | 25 | 10 | 34.0 ± 9.0 | 5.48 | 0.33 |
| K | 5 | — | 20 | 10 | 41.7 ± 7.0 | 2.27 | 0.80 |

*1: 2-ETHYLHEXYL-P-METHOXYCINNAMATE
*2: 2-HYDROXY-4-METHOXYBENZOPHENONE

Fig.26

| No. | SAMPLE | ACTIVE INGREDIENT (%) | | | | | in vitro SPF | in vivo SPF |
|---|---|---|---|---|---|---|---|---|
| | MATERIAL TYPE | Parsol MCX *1 | ASL-24 *2 | OTHERS | ULTRA-FINE TiO2 (0.03-0.05μm) | NORMAL TiO2 (0.3-0.8μm) | (MEAN± STANDARD DEVIATION) | (MEAN± STANDARD DEVIATION) |
| A | O/W EMULSION | 5 | — | — | — | — | 7.7±2.0 | 7.5±1.6 |
| B | O/W EMULSION | 4 | — | — | 6 | 6 | 15.8±3.1 | 16.2±2.3 |
| C | POWDER | — | — | — | 12 | 10 | 20.1±1.4 | 18.6±4.6 |
| D | POWDER | 3 | — | — | 10 | 18 | 18.1±1.1 | 18.9±2.9 |
| E | W/O EMULSION | 9 | 1 | 1 *3 | 3 | — | 17.9±6.6 | 19.3±4.2 |
| F | W/O EMULSION | — | — | — | 15 | — | 27.6±4.6 | 25.0±5.5 |
| G | O/W EMULSION | 7.5 | 4 | 1.5*4 | — | — | 28.3±2.1 | 29.2±4.0 |
| H | POWDER | 5 | — | — | 6 | 12 | 35.1±6.3 | 33.8±4.4 |
| I | W/O EMULSION | 5 | — | — | 10 | 9 | 38.8±1.0 | 40.5±7.8 |
| J | OIL-WAX | 5 | — | — | 20 | 10 | 40.9±3.6 | 42.2±4.4 |

METHOD AND APPARATUS FOR MEASURING ULTRAVIOLET PROTECTION EFFECTIVENESS

BACKGROUND OF THE INVENTION

1. Field of the Invention

The present invention relates to a method and apparatus for measuring ultraviolet protection effectiveness, and more particularly to a method and apparatus for obtaining in vitro SPF values having a high degree of correlation with SPF values measured on human skin (SPF—Sun Protection Factor: the degree of protectiveness provided by cosmetics against sunburn caused by exposure to ultraviolet radiation).

2. Description of the Related Art

SPF Values are used to indicate the effectiveness of sunscreen preparations, generally known as suncare products, in protecting the skin against sunburn caused by exposure to ultraviolet radiation. The SPF is an index to indicate the effectiveness in protecting the skin against sunburn from ultraviolet B radiation (that causes redness, flushing, or inflammation on the skin in short periods of time), and is defined as follows.

SPF=WITH SUNCARE PRODUCT APPLIED, UV AMOUNT NECESSARY TO CAUSE SLIGHT REDNESS (MED: MINIMUM ERYTHEMA DOSE)/WITH SUNCARE PRODUCT NOT APPLIED, UV AMOUNT NECESSARY TO CAUSE SLIGHT REDNESS (MED: MINIMUM ERYTHEMA DOSE).

A suncare product with SPF 8, for example, means that with this suncare product applied on the skin, the same degree of sunburn would be caused as an unprotected skin when the protected skin was exposed to eight times as much ultraviolet B radiation as the unprotected skin.

For the measurement of SPF values, an artificial light (solar simulator), very close to sunlight, is used since with real sunlight the value can vary from season to season and from place to place. In a commonly practiced measurement method, skin protected with a suncare product and unprotected skin are exposed to the same amounts of ultraviolet radiation, and are examined the next day to determine whether sunburn (erythema) has been caused on the skin.

In the U.S., the SPF measurement procedures are specified by Federal Register OTC monograph (1978) of FDA as follows.

1. Subjects are males and females, age 18 or older, with skin types I to III*.
2. The number of subjects is 20 or more.
3. Prescribed sunscreen preparations with SPF 4 are used as the standard sample.

The quantity of sample application is 2 mg($\mu$s)/cm$^2$.

5. The area of sample application is 20 cm$^2$ or more.
6. The time from sample application to UV irradiation is 15 minutes or more.
7. The light source used is solar UV-B light, wavelengths 290 to 320 nm, or a solar simulator close to solar light.
8. Irradiation area is 0.5 cm$^2$ or more.
9. Irradiation amount is increased by the same proportion, the proportion not exceeding 25%.
10. MED evaluation is made by a skilled person in the light 16 to 24 hours after the end of the irradiation.
11. SPF is calculated in accordance with a formula, using the MEDs of the panels obtained from the part with sample application and the part without sample application.

\* U.S. classification of skin types

Type I very easily gets sunburnt (reddish), but does not become brown.
Type II Easily gets sunburnt (reddish), and becomes slightly brown.
Type III Always becomes brown after getting sunburnt (reddish).
Type IV Does not get sunburnt (reddish) easily, but easily becomes brown.
Type V Does not get sunburnt (reddish), but becomes very brown.
Type VI Never gets sunburnt (reddish), but becomes very brown.

Using the SPF measured in accordance with the above method, the effectiveness of a product in protecting the skin from ultraviolet radiation can be evaluated objectively. However, since the cooperation of many human subjects of specific skin types is essential, the above method involves a great deal of cost and time. Therefore, for evaluation of the ultraviolet protection effectiveness of a product in the development stage, for example, it is desired to develop a measurement method that can obtain in a simple manner in vitro SPF values having high correlation with in vivo SPF values that could be obtained by the above method.

Methods such as shown in Table 1 are proposed as in vitro SPF measurement methods. The results of the evaluation of these methods are shown in Table 2.

TABLE 1

| MEASUREMENT METHOD | DESCRIPTION |
| --- | --- |
| DILUTE SOLUTION METHOD | SAMPLE DILUTED WITH ETHANOL OR OTHER ORGANIC SOLVENT IS PLACED IN A SILICA CELL AND MEASURED FOR TRANSMITTANCE OR ABSORBANCE IN 290 TO 400-nm RANGE. |
| THIN FILM METHOD | USING AN APPLICATOR, SAMPLE IS APPLIED TO A SILICA PLATE TO FORM A FILM OF UNIFORM THICKNESS, AND MEASURED FOR TRANSMITTANCE OR ABSORBANCE IN 280 TO 400-nm RANGE. |
| PEELED EPIDERMIS METHOD | USING A SOLAR SIMULATOR, SAMPLE APPLIED TO PEELED HAIRLESS MOUSE EPIDERMIS IS MEASURED FOR TRANSMITTED UV-B AMOUNT AND TRANSMITTED UV-A AMOUNT WITH A ERITHMA UV |

TABLE 1-continued

| MEASUREMENT METHOD | DESCRIPTION |
| --- | --- |
| SOLAR TEX METHOD | METER. SAMPLE IS APPLIED ON A CULTURE BARRIER OF KERATIN AND COLLAGEN, AND LEVELS OF COLOR LIBERATION AND MODIFICATION OF INTERNAL PHOTOREACTIVE BIOMATRIX ARE MEASURED. |
| DIFFEY & ROBSON METHOD | USING A XENON-ARC LAMP, UV LIGHT TRANSMITTED THROUGH SAMPLE APPLIED TO MEDICAL TAPE IS MEASURED, AND SPF IS CALCULATED USING DIFFEY & ROBSON EQUATION. |

TABLE 2

| FEATURE PREDICTION | CORRELATION WITH SPF VALUE | | | | UNKNOWN TYPE SPF PREDICTION | MEASURABLE SPF VALUE |
| --- | --- | --- | --- | --- | --- | --- |
|  | SUNSCREEN | LIQUID FD | POWDER FD | OIL FD |  |  |
| DILUTE SOLUTION METHOD | Δ | x | x | x | x | 15 |
| THIN FILM METHOD | Δ | Δ | x | x | x | 15 |
| PEELED EPIDERMIS METHOD | o | Δ | Δ | Δ | x | 30 |
| SOLAR TEX METHOD | o | Δ | Δ | Δ | x | 22 |
| DIFFEY & ROBSON METHOD | o | Δ | Δ | Δ | x | 80 |

NOTE:
x INDICATES MEASUREMENT NOT POSSIBLE.

These methods have been developed primarily for the evaluation of sunscreen preparations (sunscreen lotions and creams). When the object of measurement is limited to sunscreens, some of the methods achieve relatively high correlation with in vivo SPF values (as marked Δ and o in the column of "SUNSCREEN" in Table 2). For other types of materials than the sunscreen, however, measurements are not possible with many of the methods (as marked x in Table 2) since measurable samples cannot be prepared; even if such samples can be prepared, the correlation with in vivo SPF values is by no means satisfactory (as marked by Δ in Table 2). Furthermore, as will be described in detail later, since the relationship between the measured value and in vivo SPF value slightly varies from one material type to another, a conversion coefficient needs to be calculated for each material type from many samples of similar types, and as a result, if the material type of the sample is unknown, measurement cannot be made (Table 2). Furthermore, it is desirable that the maximum measurable SPF be as high as possible, but with many of the methods, the highest measurable SPF value is low (Table 2). Even if SPF values which are more than 20 could be measurable, they have no correlation with in vivo SPF values.

In previous methods, since it was believed that the ability of UV-A (320–400 nm) to cause erythema was extremely small (1/1000–1/15000) compared to that of UV-B (290–320 nm) and also that the former had an additive effect on the latter, the ability to cause erythema was measured for each wavelength, to calculate an erythema effectiveness, and the transmitted UV amount was multiplied by the erythema effectiveness calculated for each wavelength, to correct the erythema-inducing UV intensity (erythemal UV intensity: EUI), from which the SPF value was directly calculated. As long as such a technique is employed, it is believed that there is a limit to the correlation with in vivo SPF values and also that there is a need to use different coefficients for material types with different transmitted UV-A amounts.

SUMMARY OF THE INVENTION

It is accordingly an object of the present invention to provide a measurement method and apparatus capable of obtaining in vitro SPF values having high correlation with in vivo SPF values regardless of the material type of the sample.

It is another object of the invention to provide a measurement method and apparatus capable of obtaining in vitro SPF values having high correlation with in vivo SPF values for any material type, by performing calculation using a common coefficient independent of the material type.

It is a further object of the invention to provide a measurement method and apparatus wherein the maximum measurable SPF value is high.

To achieve the above objects, the present invention provides a method of measuring ultraviolet protection effectiveness, comprising the steps of: measuring the intensities of ultraviolet radiation at a plurality of wavelength sections of the ultraviolet radiation transmitted through a sample; calculating an erythema-inducing UV intensity by multiplying the intensities measured at said plurality of wavelength sections by erythemal effectiveness coefficients associated with the respective wavelength sections and by summing the resulting products; calculating a transmitted UV-A intensity by summing the intensities at the respective wavelength sections that lie within the wavelength range of UV-A; calculating a photoaugmentative effectiveness from said transmitted UV-A intensity; calculating an ultimate erythema-inducing UV intensity by multiplying said erythema-inducing UV intensity by said photoaugmentative effectiveness; and calculating an SPF value from said ultimate erythema-inducing UV intensity.

The invention also provides an apparatus for measuring ultraviolet protection effectiveness, comprising: means for measuring the intensities of ultraviolet radiation at a plurality of wavelength sections of the ultraviolet radiation transmitted through a sample; means for calculating an erythema-inducing UV intensity by multiplying the intensities measured at said plurality of wavelength sections by erythemal effectiveness coefficients associated with the respective wavelength sections and by summing the resulting products; means for calculating a transmitted UV-A intensity by summing the intensities at the respective wavelength sections that lie within the wavelength range of I/V-A; means for calculating a photoaugmentative effectiveness from said transmitted UV-A intensity; means for calculating an ultimate erythema-inducing UV intensity by multiplying said-erythema-inducing UV intensity by said photoaugmentative effectiveness and means for calculating an SPF value from said ultimate erythema-inducing UV intensity.

As will be described in detail later, it was quantitatively verified by the present inventor that the photoaugmentative effect of UV-A on the erythema-inducing effect of UV-B is not additive, but synergistic. According to the invention, the transmitted UV-A intensity is calculated, from which the photoaugmentative effectiveness is calculated, and then, the erythema-inducing UV intensity corrected by the erythemal effectiveness is multiplied by the photoaugmentative effectiveness, to calculate the SPF value. In this manner, the SPF having high correlation with in vivo SPF can be obtained using a common conversion equation independent of the material type.

BRIEF DESCRIPTION OF THE DRAWINGS

FIG. 17 is a diagram showing the measurement results of samples prepared for the verification of the photoaugmentative effect;

FIG. 26 is a diagram showing the results of measurements according to the second embodiment of the invention.

DESCRIPTION OF THE PREFERRED EMBODIMENTS

Figure 1:
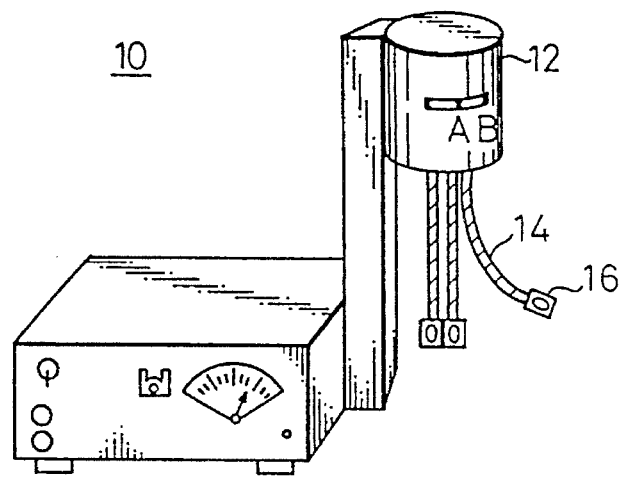
FIG. 1 is a diagram showing an overall view of a solar simulator as a light source.

FIG. 1 shows an overall view of a solar simulator 10 used as the light source in the present invention. Light from a lamp housed in a cabinet 12 is routed through a plurality of optical fibers 14 and emitted from a plurality of irradiation nozzles 16. The apparatus shown is of the same type as that used in the previously described in vivo SPF measurement method defined in FDA in the U.S.

Figure 2:
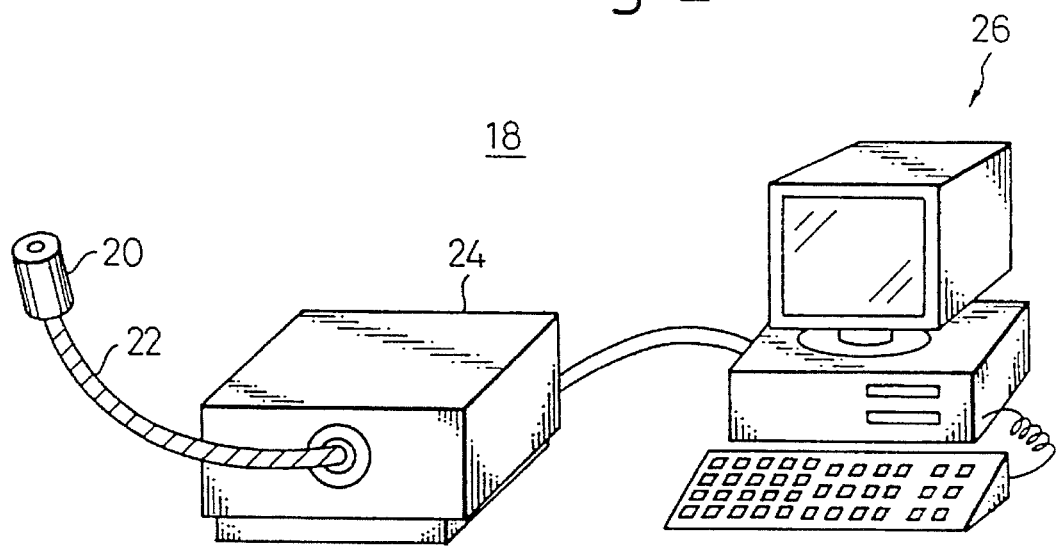
FIG. 2 is a diagram showing an overall view of a spectroradiometer at the detector end.

FIG. 2 shows an overall view of a spectroradiometer 18. Light received by a photoreceptor 20 is directed through an optical fiber 22 into a detector 24. The detector 24 examines the light in the 250 to 420 nm range at intervals of 2 nm, and converts the intensity of each wavelength into a voltage, which is then A/D converted for output. A personal computer 26 receives information on the intensity obtained at intervals of 2 nm from the detector 24, and performs operations hereinafter described to calculate the SPF value concerned.

Figure 3:
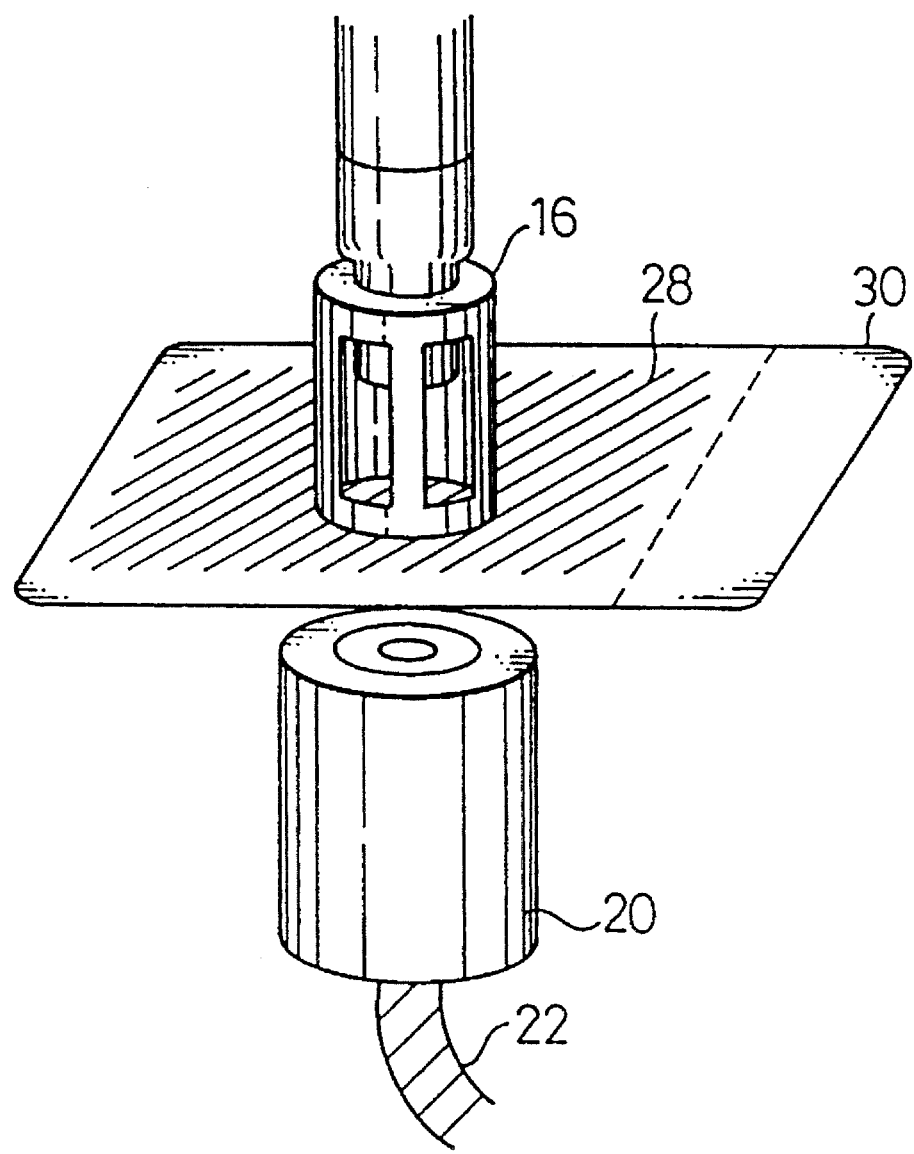
FIG. 3 is a diagram showing the positional relationship between an irradiation nozzle, a photoreceptor, and a sample.

FIG. 3 shows the positional relationship between the irradiation nozzle 16 and the photoreceptor 20 during measurement. The irradiation nozzle 16 and the photoreceptor 20 are fixed in position, spaced apart from each other by a prescribed distance, and a tape member 30 with a prescribed quantity of sample 28 applied to it is held in a fixed position at a predetermined distance from the irradiation nozzle 16. Any material transparent to ultraviolet radiation may be used as the tape member 30, but Transpore™ tape manufactured by 3M is preferable since this tape developed for medical use has numerous pores formed therein resembling the micro-features of the skin surface. To prevent the applied lotion from falling into the tape pores and reaching the back of the tape, two pieces of tape are bonded together with their adhesive faces facing each other.

Embodiment 1

Figure 4:
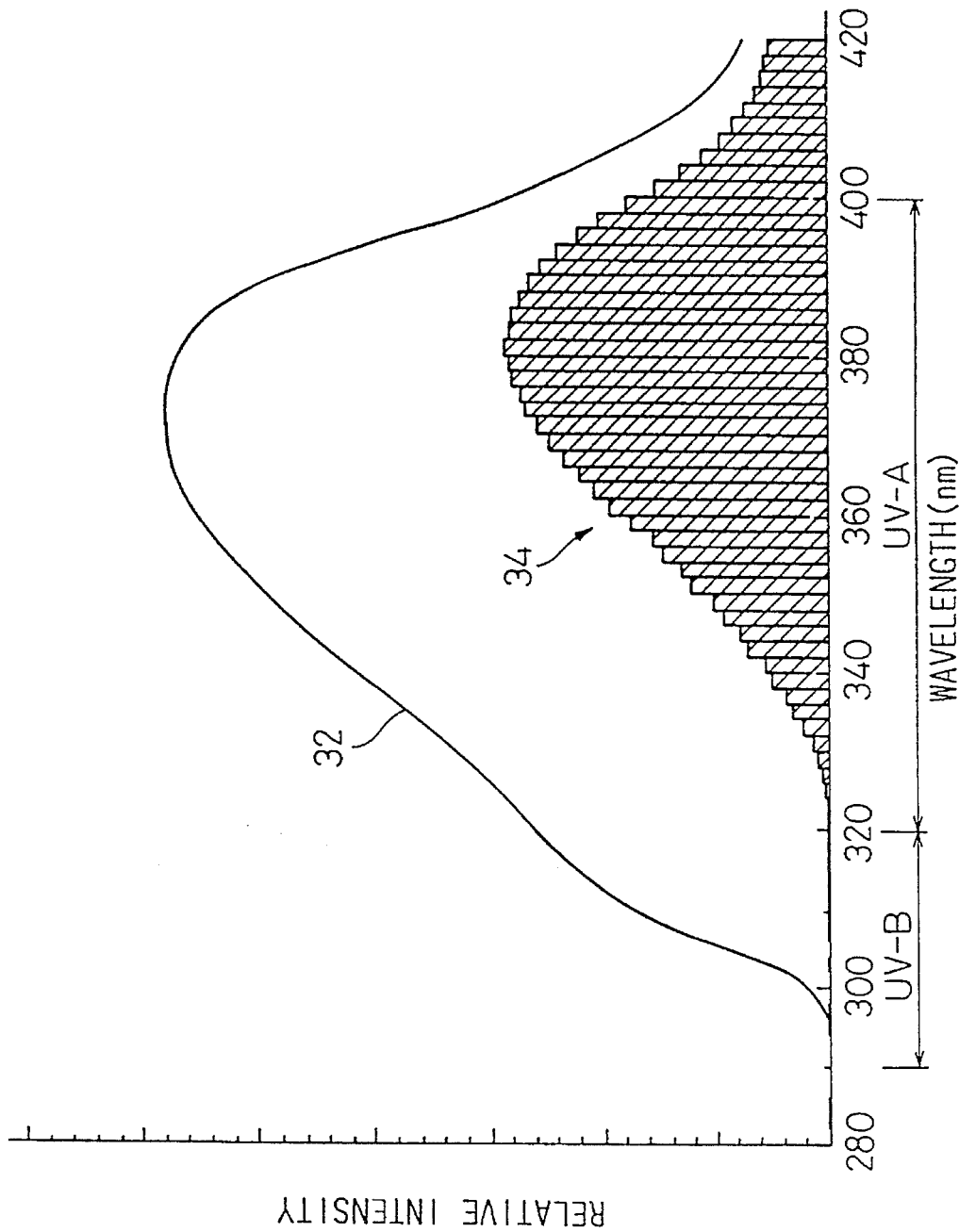
FIG. 4 is a diagram showing the spectrum of the light radiated from the solar simulator, along with the spectrum of transmitted light as an example.
Figure 5:
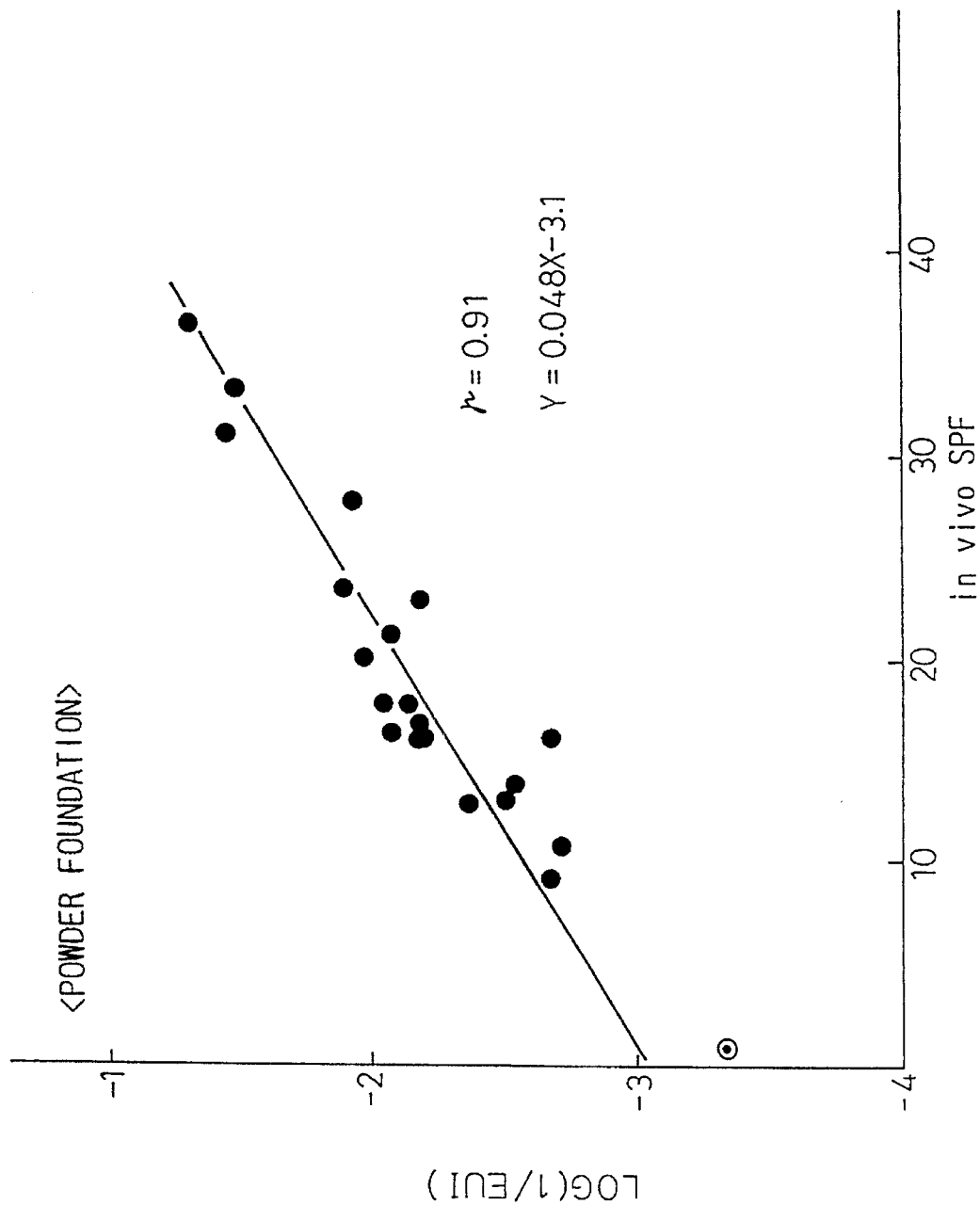
FIG. 5 is a diagram showing the correlation between EUI and in vivo SPF values for powder foundation.
Figure 6:
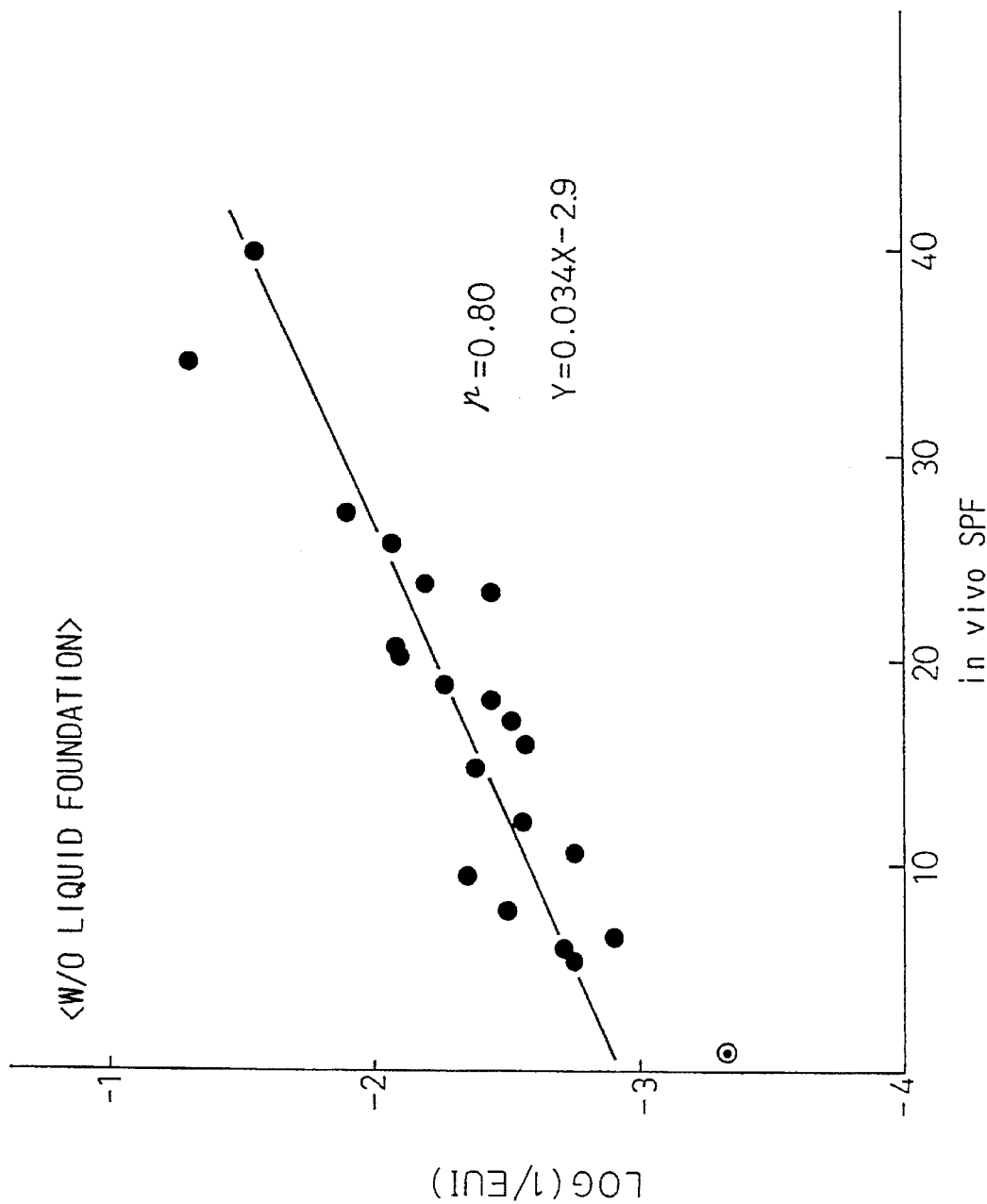
FIG. 6 is a diagram showing the correlation between EUI and in vivo SPF for W/O liquid foundation.
Figure 7:
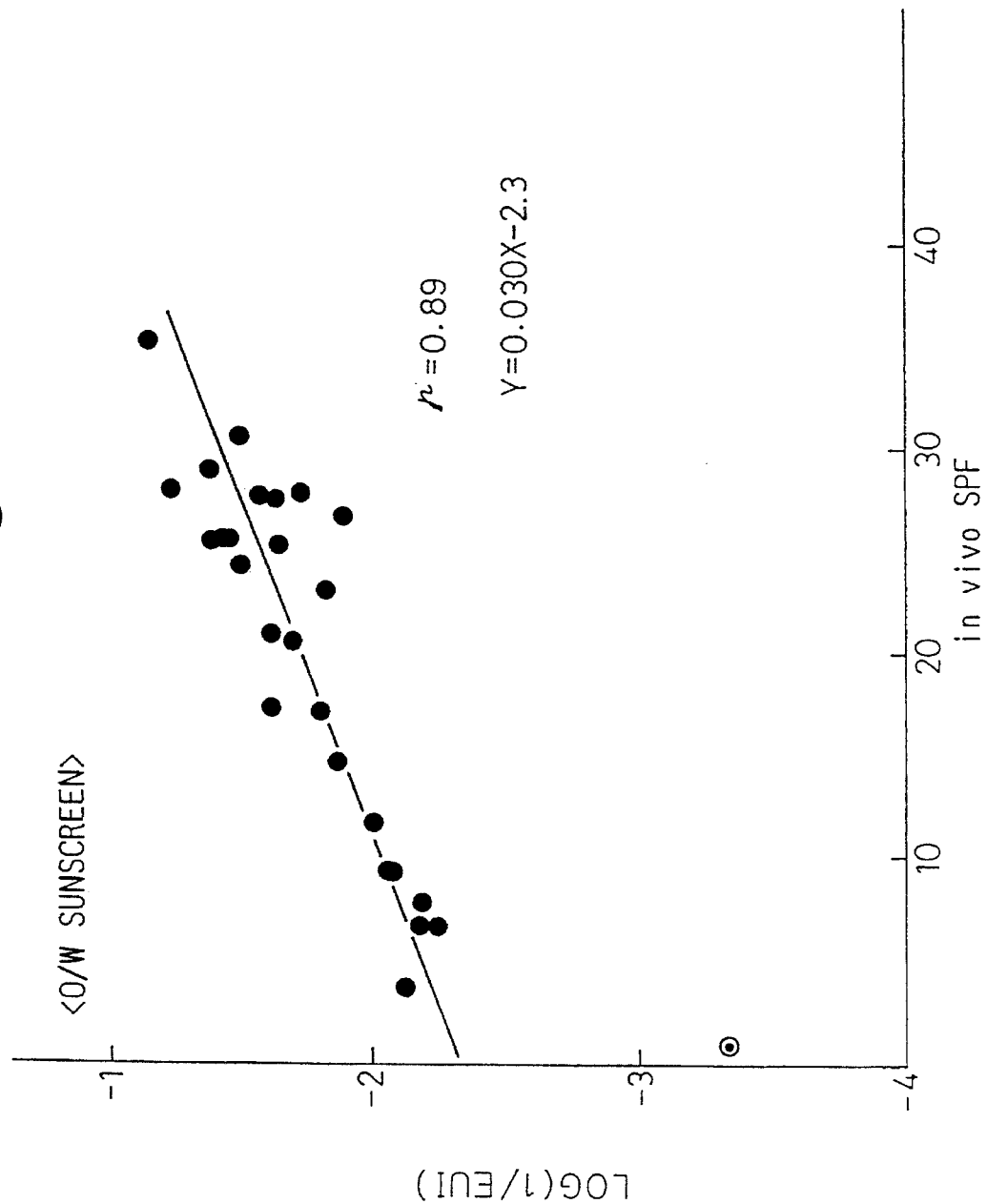
FIG. 7 is a diagram showing the correlation between EUI and in vivo SPF values for O/W sunscreen.

FIG. 4 shows the spectrum 32 of the light radiated from the solar simulator 10, along with the spectrum 34 of the light transmitted through a certain sample. The spectrum 34 of the transmitted light is shown by a bar graph, each bar representing the intensity measured at intervals of 2 nm. The measurement conditions are as follows.

(1) UV-B intensity 2.0 MED/min
(2) Radiation distance 10 mm
(3) Measurement time 500–3000 msec (adequately set according to transmitted UV intensities)
(4) Application quantity 1.0 mg/cm$^2$
(5) Sample is applied uniformly on tape by finger, and measurement is made after 15 or more minutes.

In the first embodiment of the invention, the quantity of sample application is set at 1.0 mg/cm$^2$, as compared with 2.0 mg/cm$^2$ specified FDA of the U.S., to enable measurement up to a higher SPF value.

First, in accordance with previous methods, the transmitted UV intensity $I(\lambda)$ at each wavelength $\lambda$ in the 290 to 400 nm range is multiplied by the associated erythemal effectiveness (relative coefficient associated with the ability to cause erythema) $EE(\lambda)$ shown in Table 3. Then, the sum is taken to calculate the erythemal UV intensity (EUI), ($\Sigma EE(\lambda)I(\lambda)$, and $\log(1/EUI)$ is plotted against the SPF values measured in vivo.

TABLE 3

| ERYTHEMAL EFFECTIVENESS EE ($\lambda$) | |
| --- | --- |
| $\lambda$ (nm) | EE ($\lambda$) |
| 290 – 292 | 5.2 |
| 292 – 294 | 5.1 |
| 294 – 296 | 5.0 |
| 296 – 298 | 4.9 |
| 298 – 300 | 4.7 |
| 300 – 302 | 4.4 |
| 302 – 304 | 4.0 |
| 304 – 306 | 3.8 |
| 306 – 308 | 2.7 |
| 308 – 310 | 1.0 |
| 310 – 312 | $5.0 \times 10^{-1}$ |
| 312 – 314 | $3.5 \times 10^{-1}$ |
| 314 – 316 | $2.5 \times 10^{-1}$ |
| 316 – 318 | $2.0 \times 10^{-1}$ |
| 318 – 320 | $1.5 \times 10^{-1}$ |
| 320 – 322 | $5.0 \times 10^{-2}$ |
| 322 – 324 | $2.5 \times 10^{-2}$ |

TABLE 3-continued

| ERYTHEMAL EFFECTIVENESS EE ($\lambda$) | |
| --- | --- |
| $\lambda$ (nm) | EE ($\lambda$) |
| 324 – 326 | $1.5 \times 10^{-2}$ |
| 326 – 328 | $8.0 \times 10^{-3}$ |
| 328 – 330 | $5.0 \times 10^{-3}$ |
| 330 – 400 | $2.0 \times 10^{-3}$ |

Figure 8:
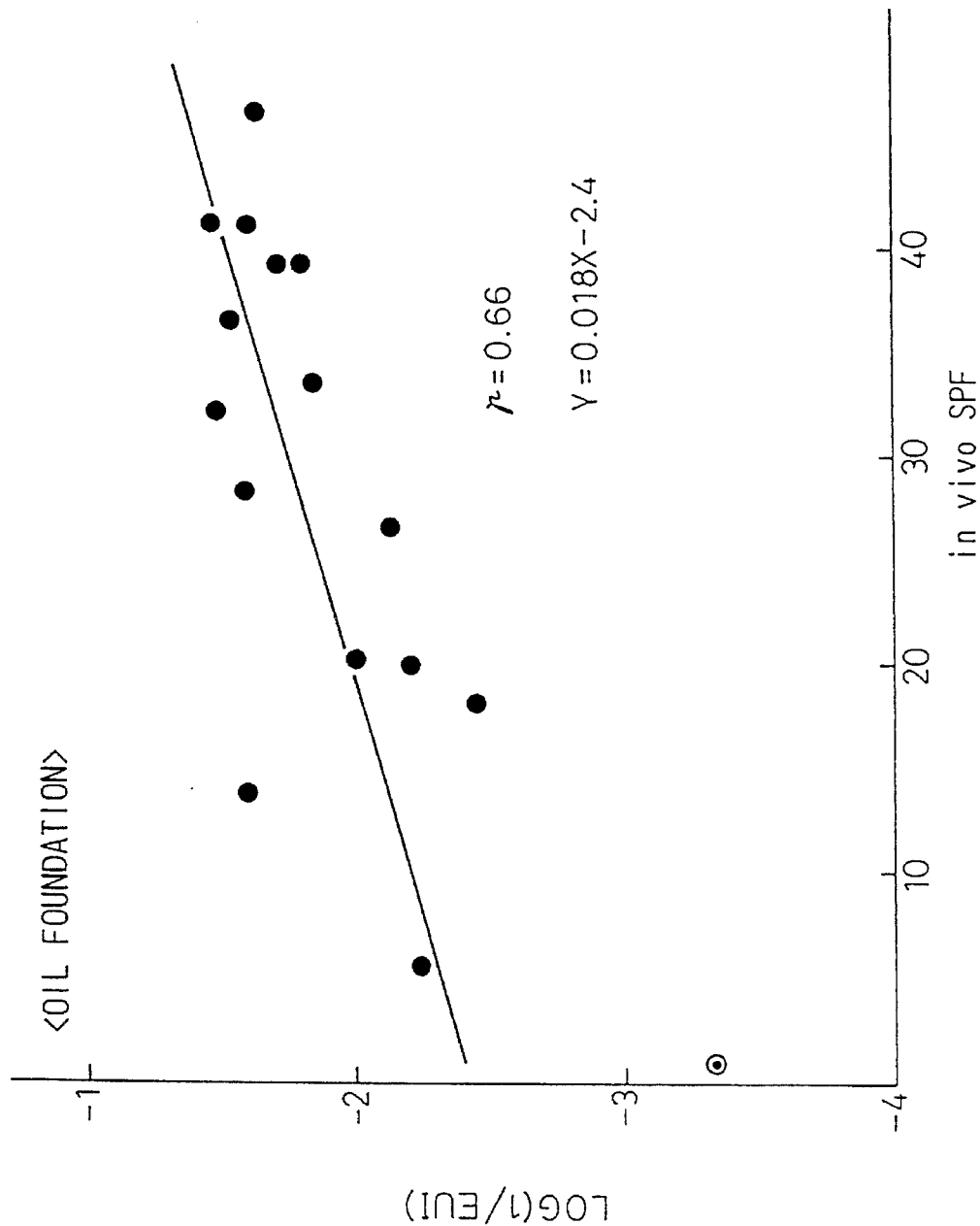
FIG. 8 is a diagram showing the correlation between EUI and in vivo SPF values for oil foundation.

FIGS. 5 to 8 are graphs plotting $\log(1/EUI)$, calculated from the erythemal UV intensity $\Sigma EE(\lambda)I(\lambda)$, against the SPF values measured in vivo for various material types. From the plots classified by material type, it can be seen that there exists a certain degree of correlation between the two, except for the case of oil foundation. However, the straight line obtained by the method of least squares for each material type differs greatly from one type to another. This means that the previous methods require the use of different calculation equations for different material types for calculation of SPF values, and also that when the material type is not known, or when one is not sure which type the material should be classified into, measurement is not possible with the previous methods. It is also shown that even when the material type is known, measurement cannot be made with good accuracy, as in the case of oil foundation (FIG. 8).

Figure 9:
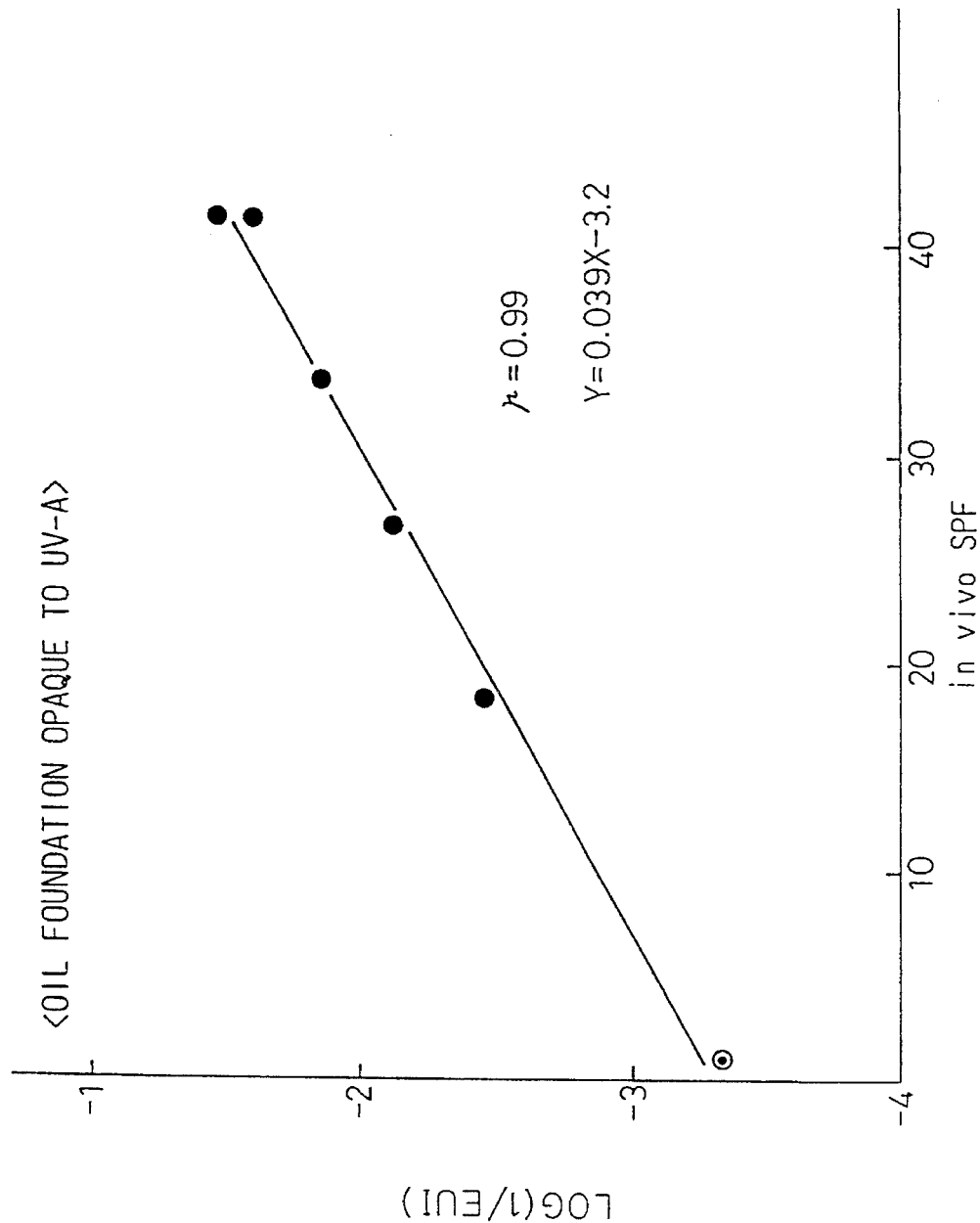
FIG. 9 is a diagram showing the correlation between EUI and in vivo SPF values for oil foundation that does not transmit UV-A.

When we look at the oil foundation for which the correlation is low, it is found that the oil foundation can be classified as transparent type, translucent type, and opaque type, according to the purpose of use. Oil foundation consists of wax, oil, and powder, and is classified by composition according to the amount of titanium oxide contained in the powder. That is, depending on the amount of titanium oxide, some transmit UV-A (320–400 nm) and some transmit very little UV-A. When the type that transmits very little UV-A was selected and a graph was plotted in the same manner as above, it was found that there exists high correlation between EUI and in vivo SPF values, as shown in FIG. 9.

From the above results, it can be shown that the influence of UV-A is not properly evaluated in the previous methods which calculate SPF directly from EUI.

Then, assuming that the effect of UV-A is synergistic, let us consider "photoaugmentative effectiveness" as a function of the UV-A amount, and assume that the value (Photoaugmentative effectiveness)×(EUI) (2) has a given relationship to in vivo SPF values regardless of the material type. When the photoaugmentative effectiveness for a sample that does not transmit UV-A is 1, the photoaugmentative effectiveness for any arbitrary sample can be roughly calculated from the following equation, using the actual EUI and the EUI value (theoretical EUI value) independent of the UV-A effect, obtained from the in vivo SPF value for that sample using the straight line in FIG. 9.

(Photoaugmentative effectiveness)=(Theoretical EUI)/(EUI)     (3)

Figure 10:
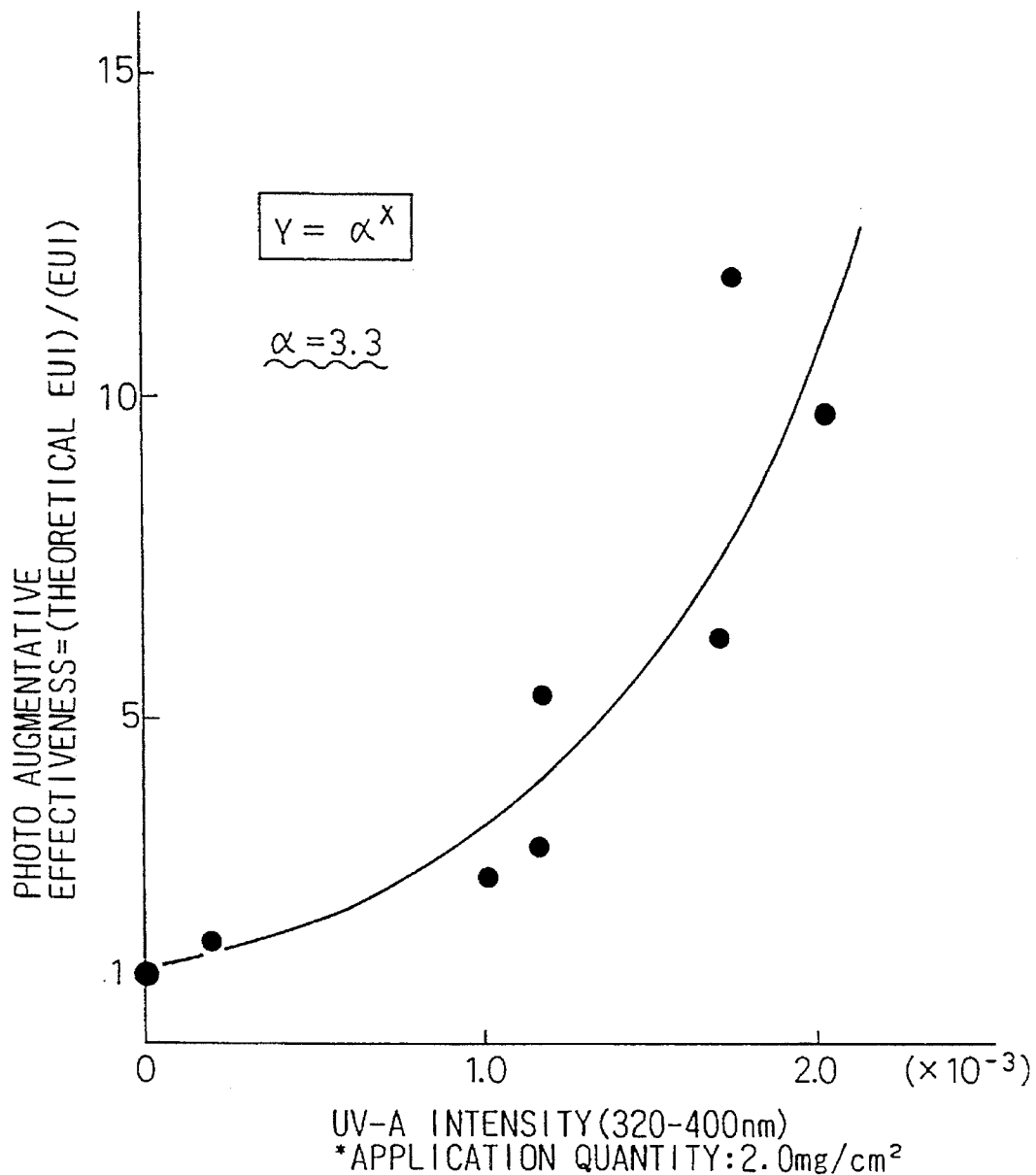
FIG. 10 is a diagram showing the relationship between the amount of UV-A and the photoaugmentative effectiveness.

FIG. 10 is a graph plotting the photoaugmentative effectiveness against the UV-A intensity for oil foundation. The UV-A intensity is the sum of the transmitted light intensities in the 320 to 400 nm range with an application quantity of 2.0 mg/cm$^2$. From FIG. 10, it can be seen that the relationship between the UV-A intensity and the photoaugmentative effectiveness is approximated by an exponential function with $\alpha$ ($\approx 3.3$) as the base.

When EUI is multiplied by this photoaugmentative effectiveness ($=3.3^{UV-A}$) and the correlations described in FIGS. 5 to 8 are reevaluated, the results shown in Table 4 are obtained. As shown, a high degree of correlation is obtained for each material type as well as for the all-material type.

TABLE 4

COMPARISON OF CORRELATION COEFFICIENTS ($\lambda$)

|  | PREVIOUS THEORY | NEW THEORY |
|---|---|---|
| O/W SUNSCREEN (N = 22) | $\gamma = 0.84$ | $\gamma = 0.91$ |
|  | (Y = 0.028X − 2.3) | (Y = 0.044X − 3.2) |
| OIL FD (N = 12 | $\gamma = 0.65$ | $\gamma = 0.96$ |
|  | (Y = 0.020X − 2.4) | (Y = 0.040X − 3.3) |
| W/O LIQUID FD (N = 16) | $\gamma = 0.85$ | $\gamma = 0.91$ |
|  | (Y = 0.030X − 2.9) | (Y = 0.053X − 3.5) |
| POWDER FD (N = 14) | $\gamma = 0.93$ | $\gamma = 0.97$ |
|  | (Y = 0.049X − 3.1) | (Y = 0.062X − 3.6) |
| ALL-MATERIAL TYPE | $\gamma = 0.71$ | $\gamma = 0.92$ |
| (N = 64) | (Y = 0.029X − 2.6) | (Y = 0.047X − 3.4) |

Further, if the relationship between the UV-A intensity and the photoaugmentative effectiveness is an exponential function, the base $\alpha$ can be calculated for each sample from the following equation.

$$\log\alpha = \{\log(\text{theoretical } EUI)/(EUI)\}/(UV\text{-}A\ \text{intensity}) \quad (4)$$

Figure 11:
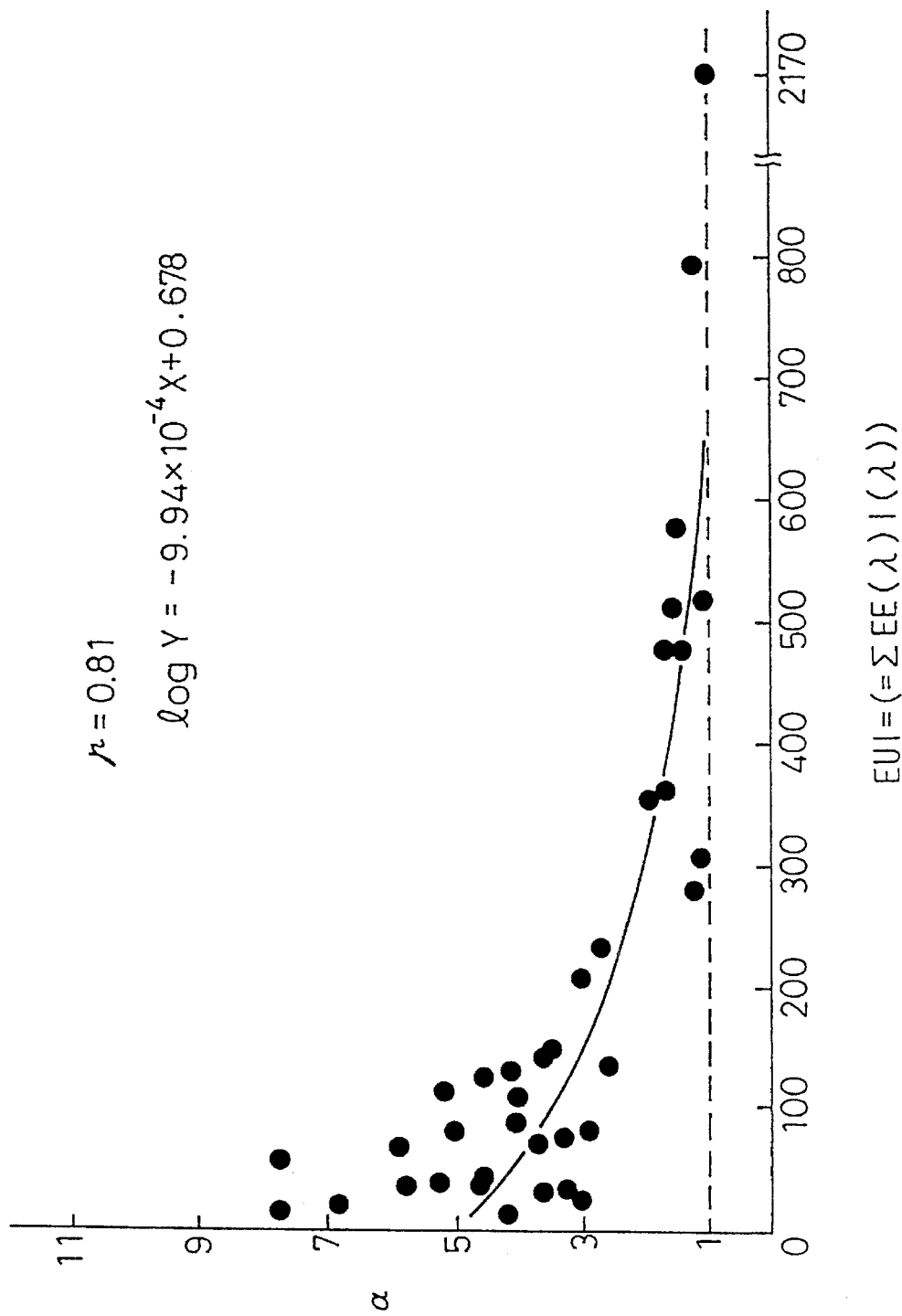
FIG. 11 is a diagram showing the relationship between EUI and the base α of the photoaugmentative effectiveness.

When this value $\alpha$ is plotted against EUI, a relation downward to the right as shown in FIG. 11 is obtained, This explains that the photoaugmentative effect of UV-A acts strongly when the transmitted UV-B intensity is relatively small, and decreases as the transmitted UV-B intensity increases. This relation can be approximated by $$\log\alpha = -9.94 \times 10^{-4} \times \Sigma EE(\lambda)I(\lambda) + 0.678 \quad (5)$$

Therefore, a more accurate photoaugmentative effectiveness is given by $$10^{**}\{(-9.94 \times 10^{-4} \times \Sigma EE(\lambda)I(\lambda) + 0.678) \times (UV\text{-}A\ \text{intensity})\} \quad (6)$$

(** means raising to power)

When the correlation between EUI multiplied by this photoaugmentative effectiveness and in vivo SPF values is evaluated, the results shown in Table 5 are obtained. As can be seen, a higher correlation is obtained for each material type, and also, the equation expressing the correlation is more or less the same for each material type.

TABLE 5

|  | PREVIOUS THEORY | NEW THEORY | ULTIMATE THEORETICAL EQUATION |
|---|---|---|---|
| O/W SUNSCREEN | $\gamma = 0.84$ | $\gamma = 0.91$ | $\gamma = 0.93$ |
| (N = 22) | (Y = 0.028X − 2.3) | (Y = 0.044X − 3.2) | (Y = 0.040X − 3.2) |
| OIL FD | $\gamma = 0.65$ | $\gamma = 0.96$ | $\gamma = 0.97$ |
| (N = 12) | (Y = 0.020X − 2.4) | (Y = 0.040X − 3.3) | (Y = 0.041X − 3.3) |
| W/O LIQUID FD | $\gamma = 0.85$ | $\gamma = 0.91$ | $\gamma = 0.94$ |
| (N = 16) | (Y = 0.030X − 2.9) | (Y = 0.053X − 3.5) | (Y = 0.040X − 3.2) |
| POWDER FD | $\gamma = 0.93$ | $\gamma = 0.97$ | $\gamma = 0.98$ |
| (N = 14) | (Y = 0.049X − 3.1) | (Y = 0.062X − 3.6) | (Y = 0.054X − 3.4) |
| ALL-MATERIAL | $\gamma = 0.71$ | $\gamma = 0.92$ | $\gamma = 0.94$ |
| TYPE (N = 64) | (Y = 0.029X − 2.6) | (Y = 0.047X − 3.4) | (Y = 0.041X − 3.2) |

Figure 12:
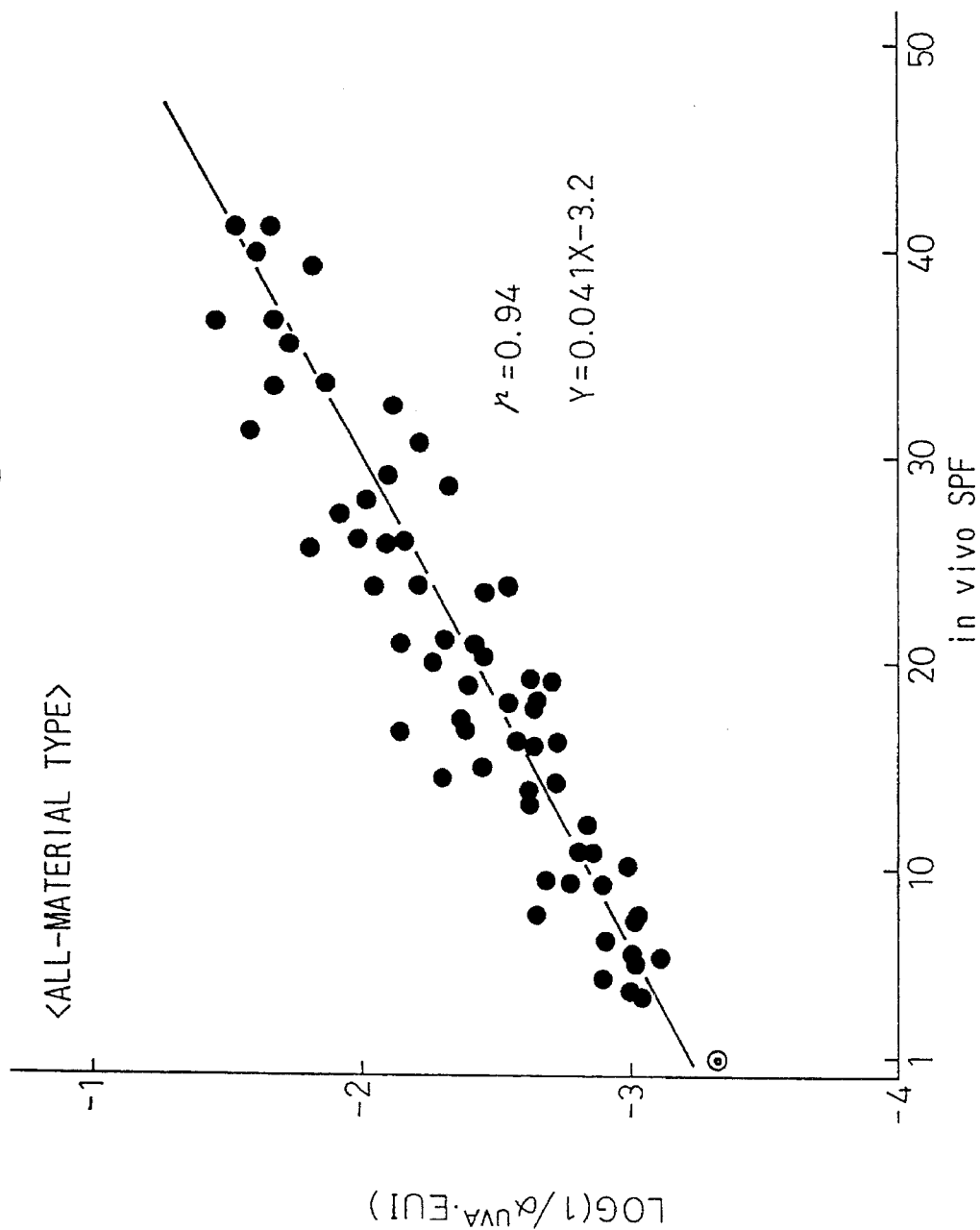
FIG. 12 is a diagram showing the correlation between EUI according to the invention and in vivo SPF values.

Furthermore, high correlation is obtained for the all-material type, the straight line having a slope of 0.041 and an intercept at −3.2, as shown in FIG. 12. Therefore, the in vitro SPF value, according to the present invention, can be calculated using the same conversion equation shown below.

$$\text{in vitro } SPF = \frac{3.2 + \log\left\{1/(\text{PHOTOAUGMENTATIVE EFFECTIVENESS})\left(\sum_{290}^{400} EE(\lambda)I(\lambda)\right)\right\}}{0.041} \quad (7)$$

$$= \frac{3.2 + \log \left\{ 1/\sum_{290}^{400} EE(\lambda)I(\lambda) \cdot 10^{(-9.97\times10^{-4}\times\sum_{290}^{400} EE(\lambda)I(\lambda)+0.678)\cdot\sum_{320}^{400} I(\lambda)} \right\}}{0.041}$$

Figure 13:
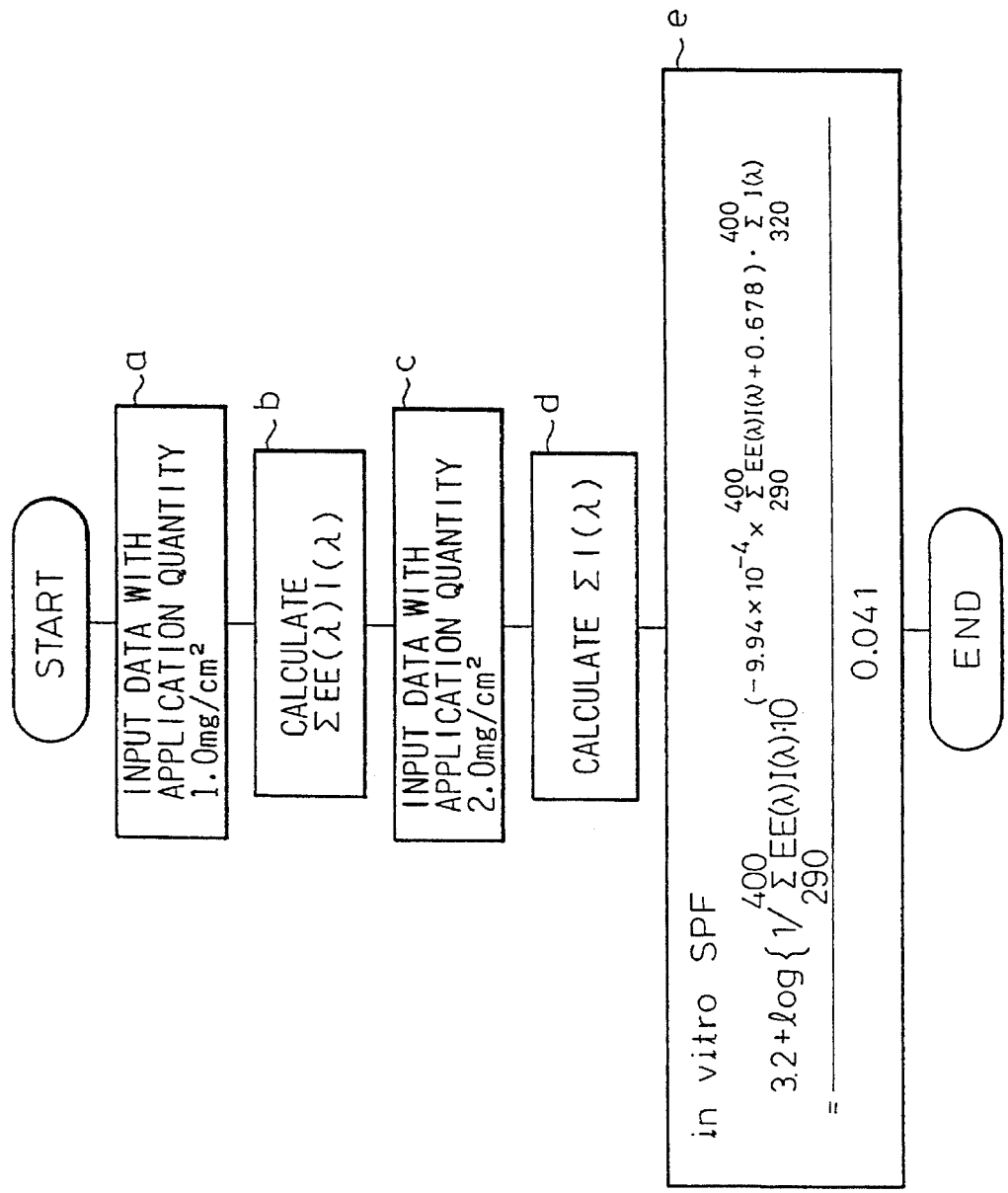
FIG. 13 is a flowchart illustrating an in vitro SPF measuring procedure according to a first embodiment of the invention.

FIG. 13 is a flowchart illustrating the processing performed by the personal computer 26 (FIG. 2) used in the SPF measuring apparatus according to the first embodiment of the invention.

First, measurement results $I(\lambda)$ with an application quantity of 1.0 mg/cm$^2$ are input from the detector 24 (step a), and $\Sigma EE(\lambda)I(\lambda)$, i.e., EUI, is calculated by multiplying the result for each wavelength section by the erythemal effectiveness $EE(\lambda)$ and by summing the elements from $\lambda=290$ to 400 nm (step b). Next, measurement results $I(\lambda)$ with an application quantity of 2.0 mg/cm$^2$ are input (step c), and the UV-A intensity $\Sigma I(\lambda)$ is calculated by summing the elements from $\lambda=320$ to 400 nm (step d). Then, using equation (7), the in vitro SPF value is calculated (step e).

When the application quantity according to the measurement method defined in FDA of the U.S. is 2.0 mg/cm$^2$, the application quantity for calculating EUI= $\Sigma EE(\lambda)I(\lambda)$ in the above procedure is set at 1.0 mg/cm$^2$ so that an even higher SPF value can be measured in vitro. Measurement up to SPF 50 or more is thus made possible. If the sample application quantity is the same for the calculation of $\Sigma I(\lambda)$ as for $\Sigma EE(\lambda)I(\lambda)$, the SPF value can be calculated in a single measurement process.

Embodiment 2

In this embodiment, the sample application quantity for the measurement of EUI and UV-A intensity is both set at 2.0 mg/cm$^2$ to match the in vivo measurement, and the in vitro SPF value is calculated in accordance with a calculation equation determined by a more theoretical approach to the erythemal response, as described hereinafter.

The SP value is the ratio of the time (t) required to reach the minimum erythemal dose (MED) when sunscreen is applied to that when no sunscreen is applied, and is expressed as $$SPF = t/t_o \qquad (8)$$

where $t_o$ is the time that would be required to reach MED when no sunscreen was applied.

The effective UV light that causes erythema directly in human skin is given by multiplying the sunscreen-transmitted UV spectrum by the erythemal relative effectiveness shown in Table 3. Therefore, the effective erythemal UV intensity (EUI) can be expressed by $$EUI = \Sigma EE(\lambda)I(\lambda) \qquad (9)$$

where $I(\lambda)$ represents the transmitted UV intensity at each wavelength detected by the spectroradiometer when the sunscreen is applied, and $EE(\lambda)$ represents the relative effectiveness associated with the wavelength that causes the erythemal response.

On the other hand, the minimum erythemal dose is the product of the time (t) required to reach MED and the UV intensity (equation (9)) that has acted on the skin, and for the same person the minimum erythemal dose should be essentially constant. Hence, the following equation holds.

$$t_o \Sigma EE(\lambda)I_o(\lambda) = t\Sigma EE(\lambda)I(\lambda) \qquad (10)$$

where $I_o(\lambda)$ represents the transmitted UV intensity when no sunscreen is applied.

From equations (8) and (10), the following equation holds.

$$SPF = \Sigma EE(\lambda)I_o(80)/\Sigma EE(\lambda)I(\lambda) \qquad (11)$$

That is, $\Sigma EE(\lambda)I_o(\lambda)$ can be regarded as a constant since it remains constant as long as the luminous intensity of the light source remains constant. Accordingly, we investigated the biological phenomena and effects regarding the erythemal response by studying and analyzing the relationship between SPF and $1/\Sigma EE(\lambda)I(\lambda)$ from equation (11).

Sunscreens (N=80) of all material types (W/O and O/W emulsion types, powder type, and oil-wax type) were evaluated.

Figure 14:
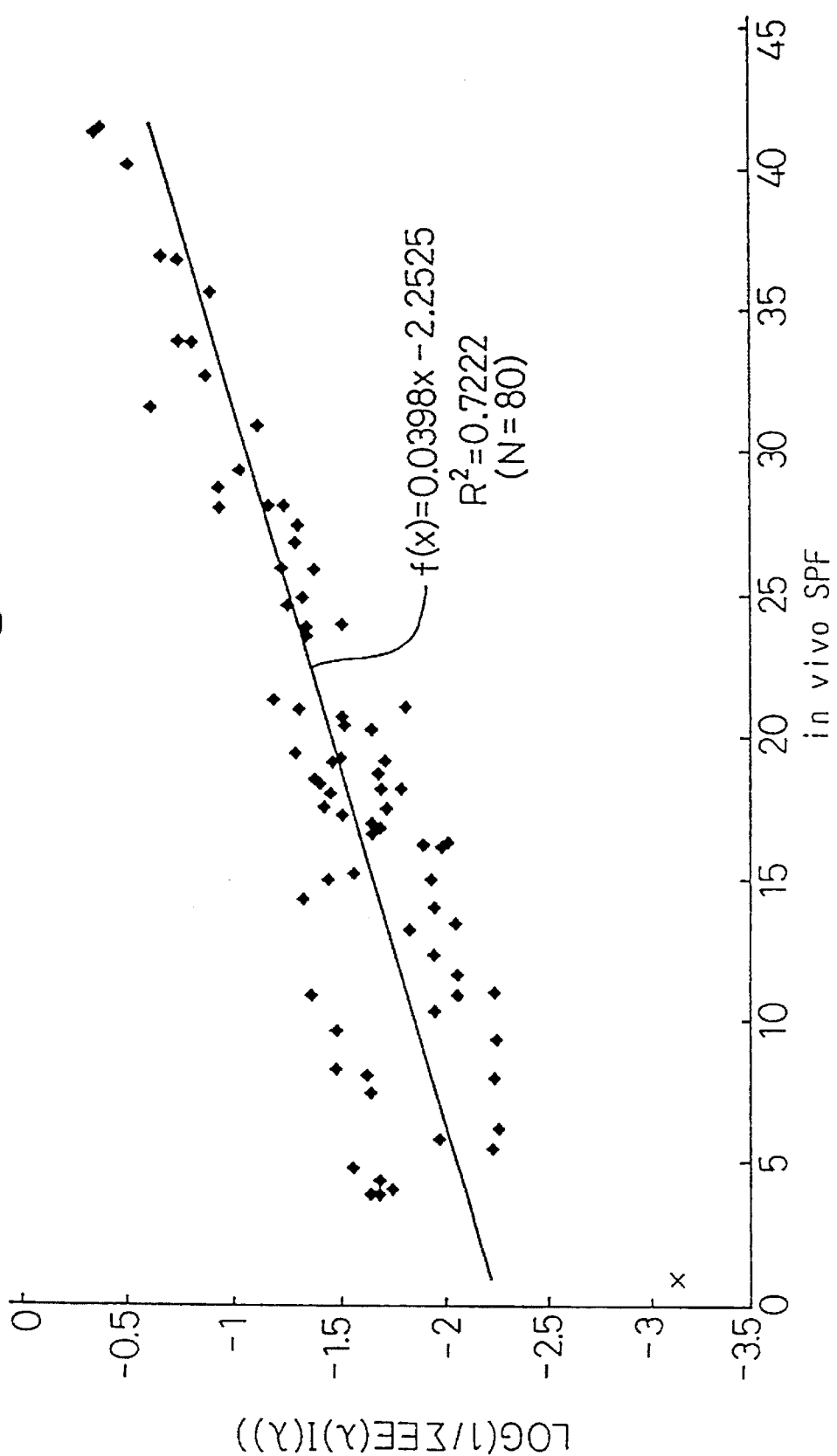
FIG. 14 is a diagram showing the relationship between EUI and in vivo SPF values for sunscreens of various material types.

FIG. 14 is a graph plotting $\log(1/\Sigma EE(\lambda)I(\lambda))$ against the SPF. In the figure, an "X" mark indicates the results without sunscreen application. From FIG. 14, it was found that for all samples there existed a certain degree of correlation between $\log(1/\Sigma EE(\lambda)I(\lambda))$ and in vivo SPF. This means that the SPF value can be predicted to some extent from the effective erythemal UV intensity (EUI) calculated by using the relative effectiveness coefficients associated with the erythema-inducing wavelengths.

Figure 15:
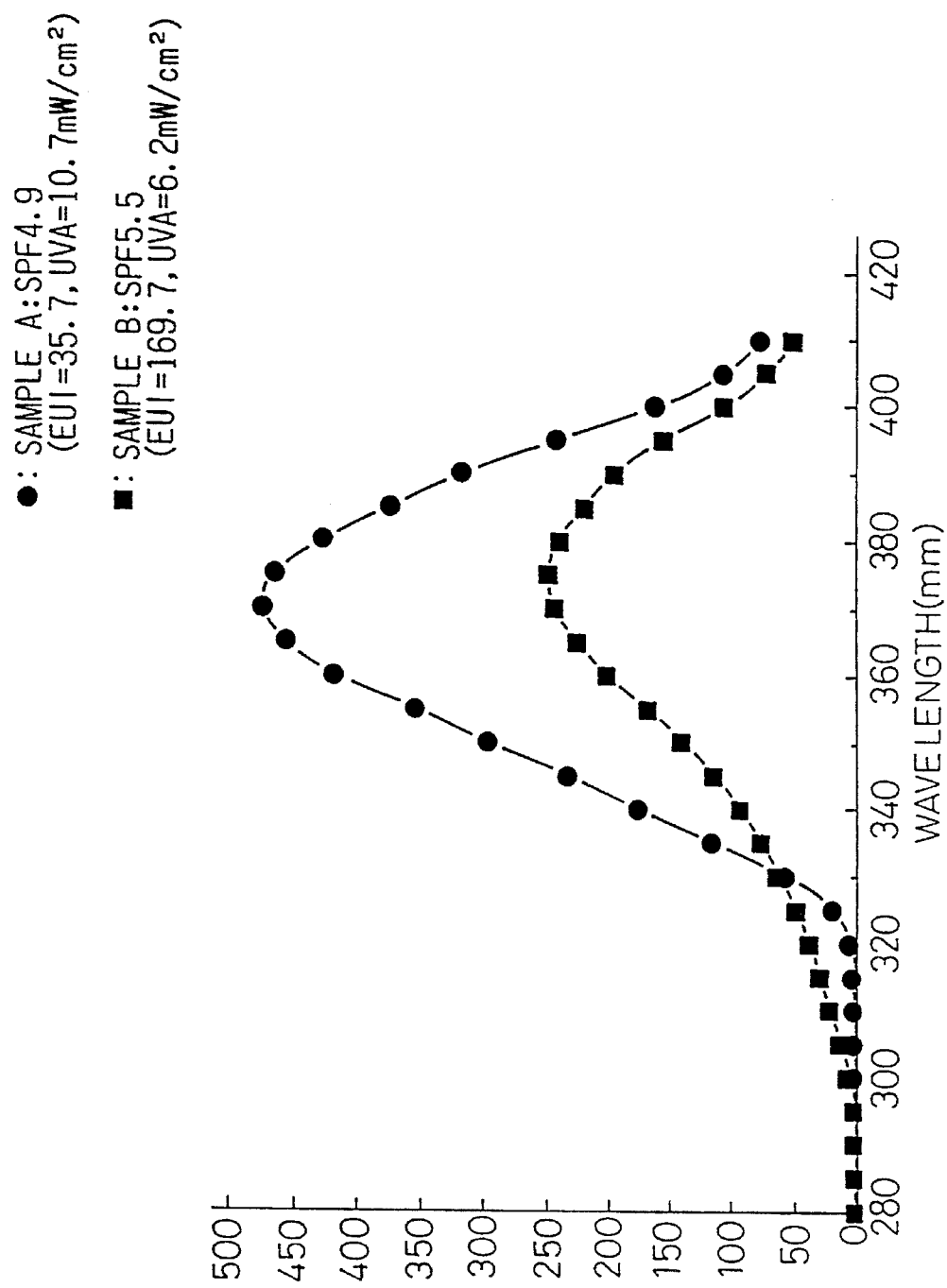
FIG. 15 is a diagram showing the transmitted UV spectra of two typical sunscreens of the same material type with similar SPF values.

Furthermore, careful observation of the transmitted UV spectra for all the samples scattered across the graph revealed that the transmitted UV spectrum differed greatly between samples located in the upper part of the graph and those located in the lower part. FIG. 15 shows the transmitted UV spectra of typical sunscreens of the same W/O emulsion type with similar SPF values. Sample A (SPF=4.9) Shown in FIG. 15 is located in the upper part of the graph, while sample B (SPF=5.5) is located in the lower part of the graph. Hence we suspected that there was a certain relationship between the transmitted UV-A intensity of the sunscreen and its position on the graph.

Figure 16:
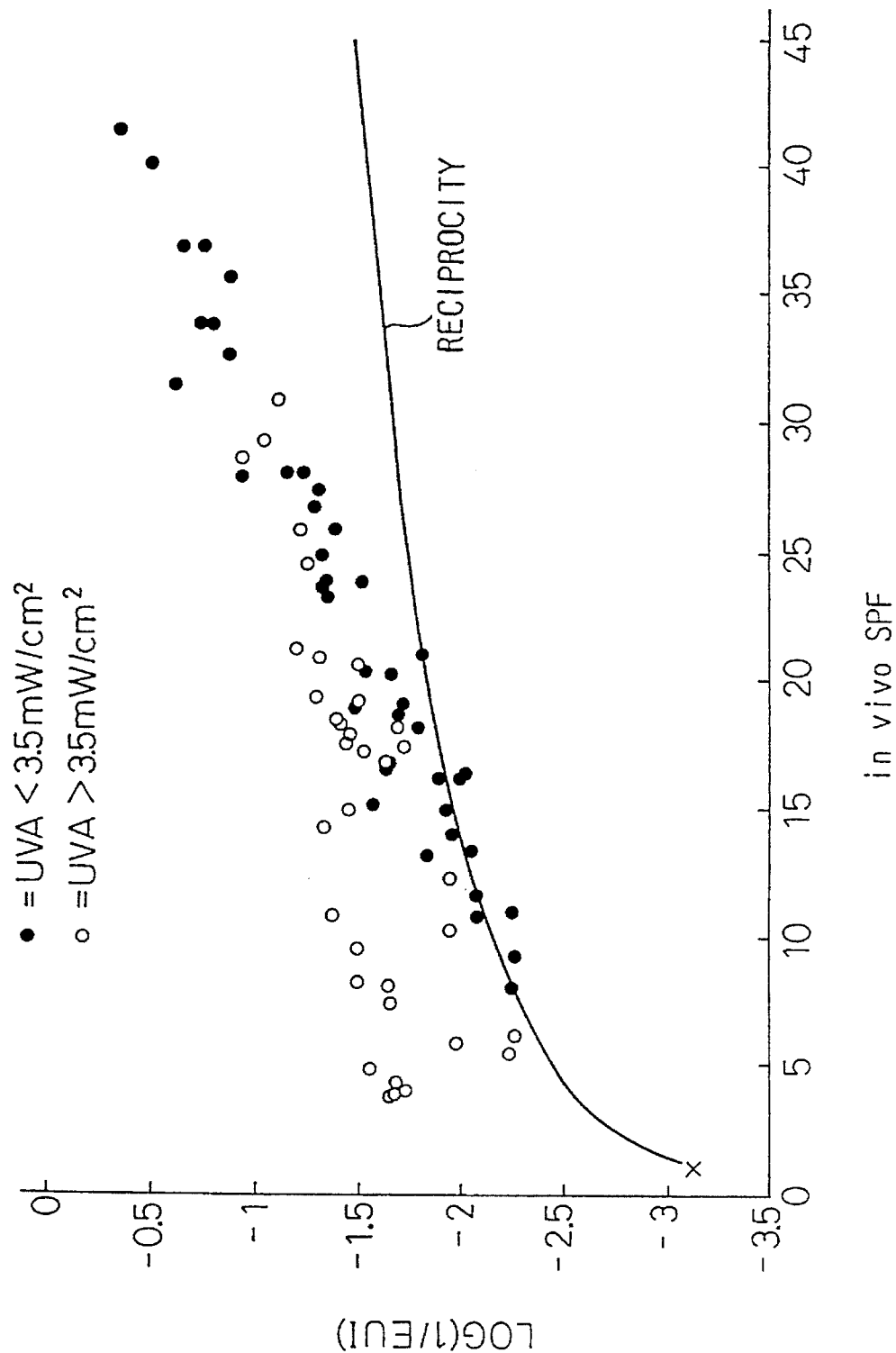
FIG. 16 is a diagram showing measurement points classified according to the magnitude of the UV-A intensity.

Accordingly, we classified the samples shown in FIG. 14 into two groups, one consisting of samples with transmitted UV-A intensities greater than 3.5 mW/cm$^2$ and the other consisting of samples with transmitted UV-A intensities smaller than 3.5 mW/cm$^2$. The result of the classification is shown in FIG. 16. As a result, it was confirmed that in the region below SPF 20, samples in the higher transmitted UV-A intensity group are located in the upper part of the graph, while those in the lower transmitted UV-A intensity group are clustered in the lower part of the graph. This suggests that the sunscreen transmitted UV-A is related in some way to the SPF value, or more specifically, to the erythemal response caused primarily by UV-B on the skin.

Figure 18:
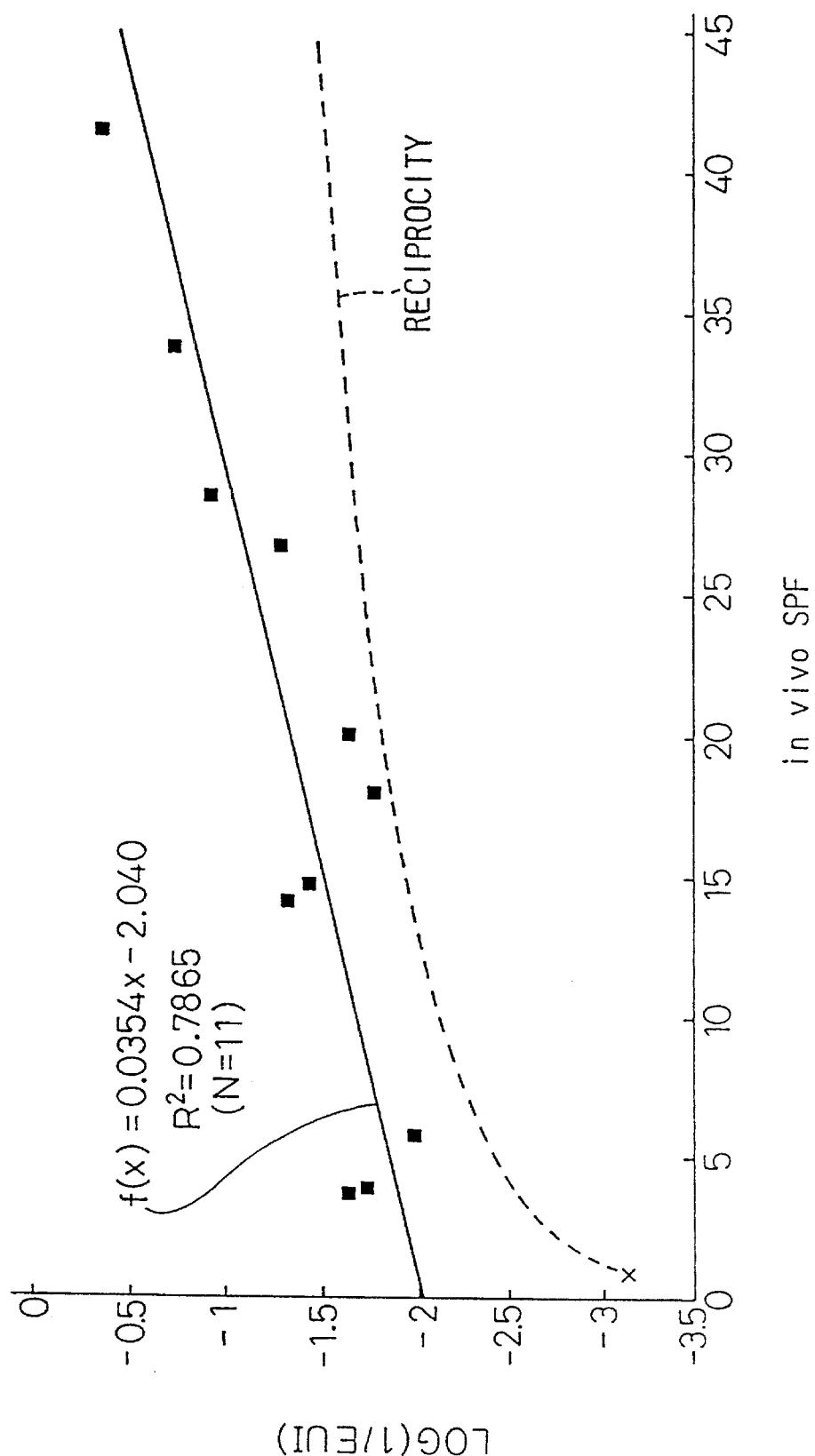
FIG. 18 is a diagram showing the relationship between EUI and in vivo SPF for the samples shown in FIG. 17.

Kligman et al. suggested the photoaugmentative effect of UV-A radiation (Willis, I., Kligman, A. M. and Epstein, J., Effects of long ultraviolet rays on human skin: Photoprotective of photoaugmentative? J. Invest. Dermatol., 59,416–420 (1972); Kaidbey, K. H. and Kligman, A. M., Further studies of photoaugmentation in humans: Phototoxic reactions. J. Invest. Dermatol., 65,472–475 (1975)). This means that the radiation amount (minimum erythemal dose: MED) of UV-B is lowered by UV-A radiation. We focused our attention on the photoaugmentative effect of UV-A. For accurate evaluation of the UV-A photoaugmentative effect, it is necessary to minimize the effects caused by differences in UV protection ability between different sunscreen material types and by the difference between the human skin and the substrate. Accordingly, sunscreens of oil-wax type relatively insensitive to the effect of the substrate were used as UV filters. Various ultraviolet absorbers and dispersants were mixed into these oil-wax type sunscreens in varying proportions to provide them with different transmitted UV spectra. The oil-wax type sunscreen provides an excellent UV filter since this type of sunscreen allows a uniform and stable mixture of various ultraviolet absorbers and dispersants and is relatively insensitive to the surface condition of the substrate (e.g., the degree of surface irregularity, affinity for water, affinity for lipids, etc.) by its oil and wax compositions. FIG. 17 shows the results of measurement of the SPF values, EUI values ($\Sigma EE(\lambda)I(\lambda)$), and transmitted UV-A intensities for these sunscreen samples. FIG. 18 shows a graph plotting EUI against SPF. As a result, the effect of the transmitted UV-A was observed, as in the example shown in FIG. 14.

Here, when we consider the photoaugmentative effect of UV-A suggested by Kligman, the above indicates a decrease in the minimum erythemal dose (MED) primarily for UV-B. This means that UV-A acted on the skin and increased the skin sensitivity to UV-B. Since the erythemal response caused to the skin is always the same in the nature of the phenomenon, the above is the same as saying that UV-B is augmented by UV-A radiation, when viewed from the skin. For evaluation of the photoaugmentative effect, therefore, it is necessary to investigate how much UV-B is augmented by UV-A radiation.

When "reciprocity" holds, equation (12) is derived by transforming equation (11).

$$\Sigma EE(\lambda)I(\lambda)=\Sigma EE(\lambda)I_o(\lambda)/SPF \quad (12)$$

Figure 19:
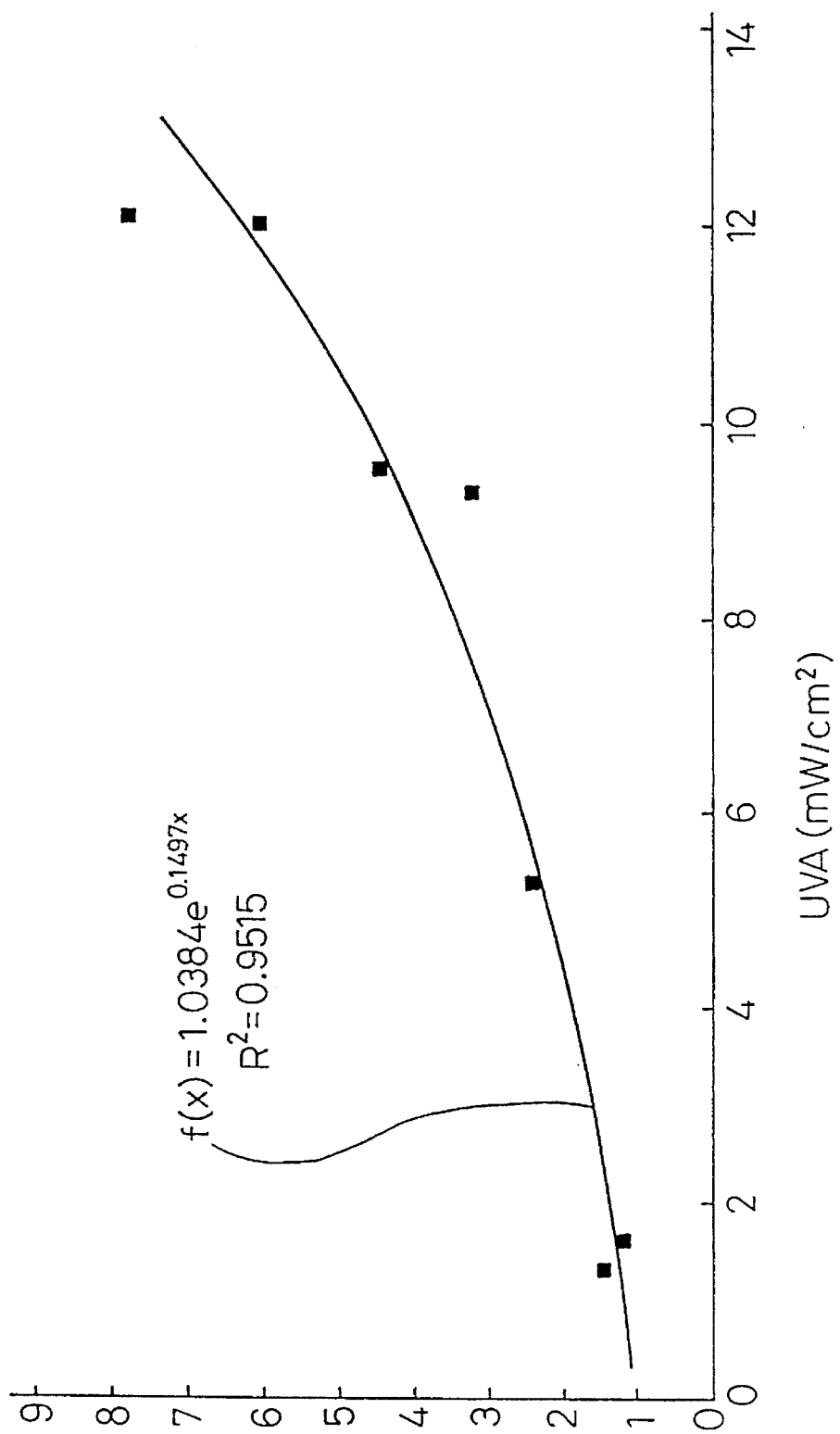
FIG. 19 is a diagram showing the relationship between the UV-A intensity and the photoaugmentative effect.

Now, when no sunscreen is applied, since the EUI value $\Sigma EE(\lambda)I_o(\lambda)$ is constant, the theoretical EUI value necessary to cause an erythemal response can be calculated by substituting the value of the constant $\Sigma EE(\lambda)I_o(\lambda)$ ($\approx 1350$) and each in vivo SPF value into equation (12). (In FIGS. 16 and 18, X marks indicate the EUI value (the value of $\log(1/\Sigma EE(\lambda)I_o(\lambda))$) when no sunscreen is applied (SPF=1), and the solid and dotted lines indicate the theoretical EUI value (the value of $\log(1EUI_{TH})$) calculated from equation (12) for each in vivo SPF value and are hereinafter referred to as the reciprocity curve.) Therefore, by evaluating the relationship of the ratio of the actual measured EUI value of a sample to the theoretical value almost insusceptible to the effect of the transmitted UV-A, with the transmitted UV-A, the photoaugmentative effect for the sample can be verified. FIG. 19 shows the photoaugmentative effect of the oil-wax type sunscreens. It can be seen from FIG. 19 that the photoaugmentative effect is an exponential function of the transmitted UV-A intensity. From the graph, the base $\alpha$ of the exponential function having the relation defined by the following equation (13) is derived.

Theoretical EUI value/actual measured EUI value=

$$\alpha^{UVA} \quad (13)$$

Hereinafter, $\alpha^{UVA}$ is referred to as the photoaugmentative effectiveness and $\alpha$ as the base of the photoaugmentative effectiveness.

Figure 20:
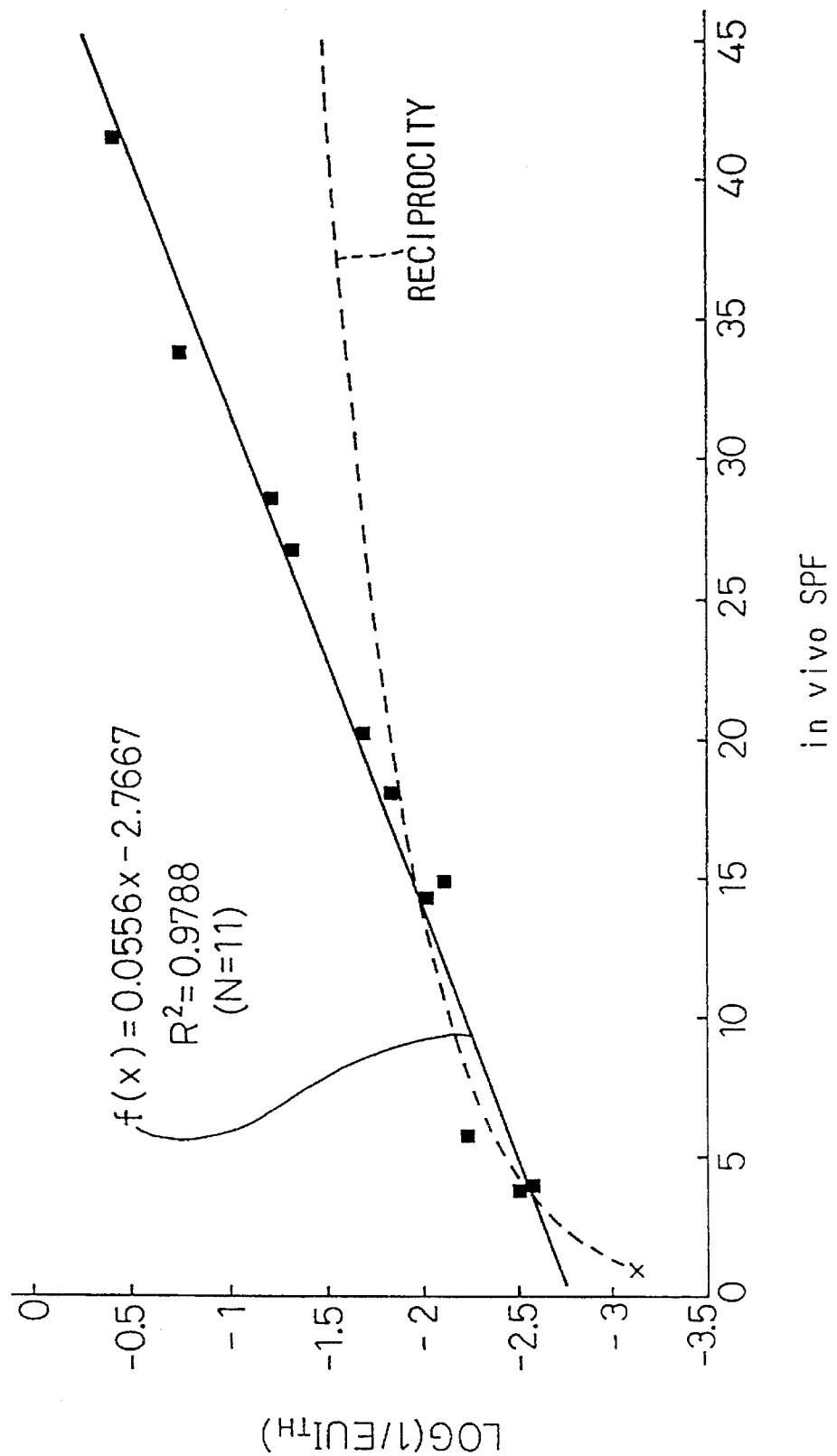
FIG. 20 is a diagram showing the relationship between $EUI_{TH}$ with the photoaugmentative effect incorporated and in vivo SPF values.
Figure 21:
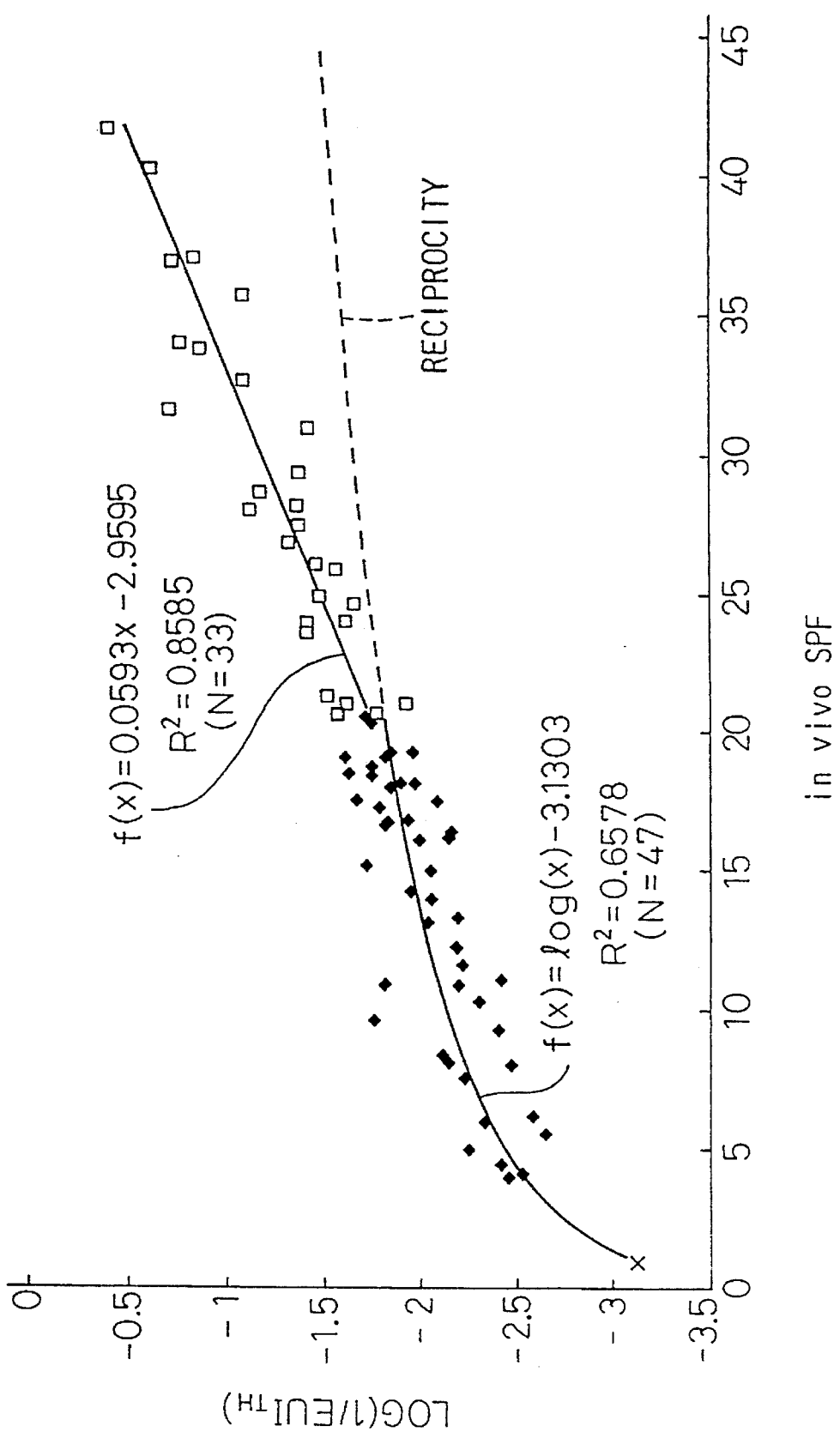
FIG. 21 is a diagram showing the relationship between $EUI_{TH}$ and in vivo SPF values for sunscreens of various material types.
Figure 22:
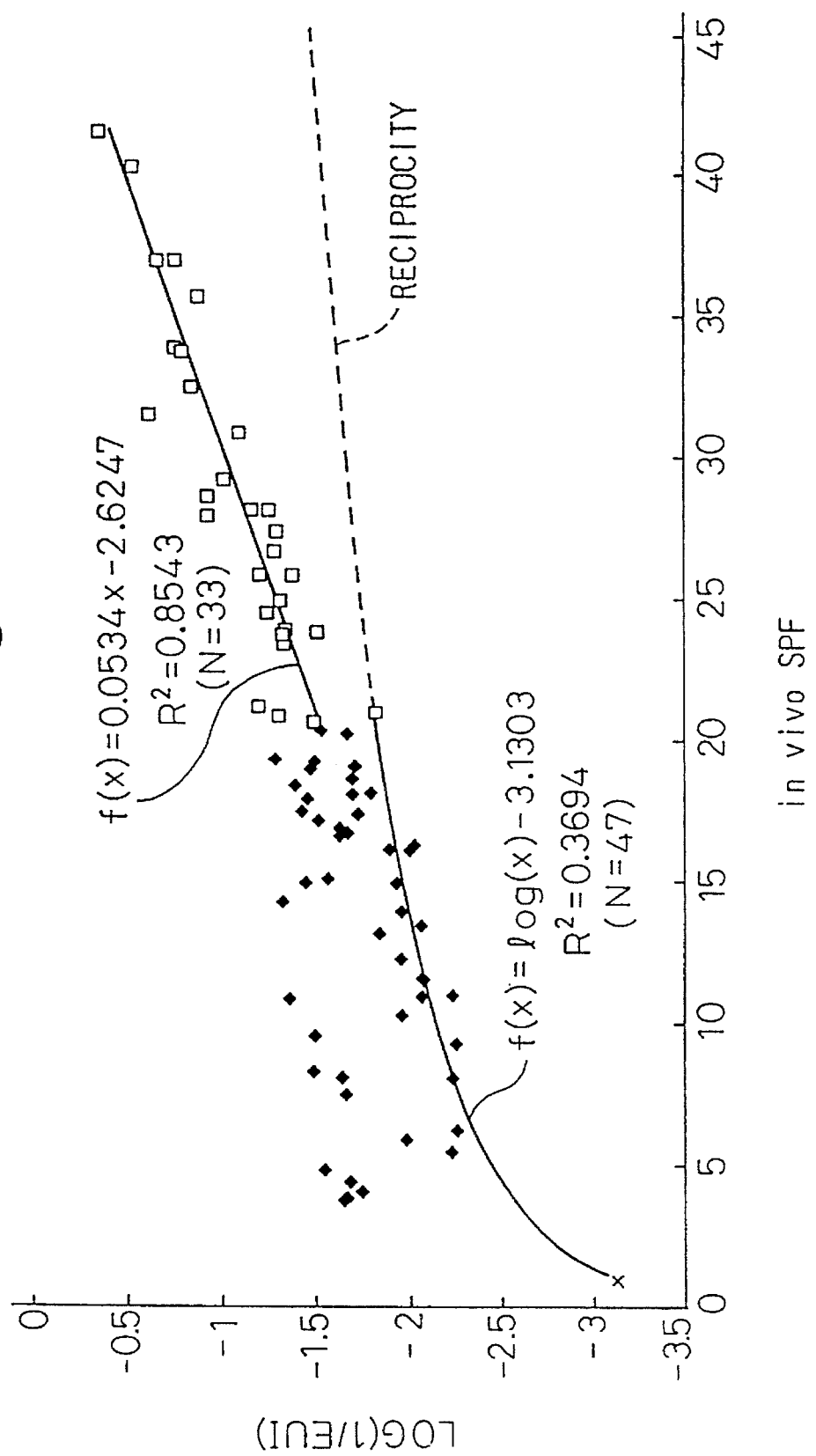
FIG. 22 is a diagram showing the relationship between EUI and in vivo SPF values for sunscreens of various material types.

From equation (13), the theoretical EUI value ($EUI_{Th}$) considered to cause an erythemal response by the UV-A photoaugmentative effect is calculated. Accordingly, we examined the relationship between the $EUI_{Th}$ values with the UV-A photoaugmentative effect incorporated and the SPF values for the oil-wax type sunscreens (FIG. 20). The dotted line in FIG. 20 indicates the reciprocity curve. Compared to the example shown in FIG. 18, the correlation coefficient shows a higher value ($R^2=0.98$), which suggests the presence of the photoaugmentative effect of UV-A. It is also shown that the reciprocity rule holds for SPP below 20 but does not hold for SPF above 20. This suggests the presence of a different biological effect relating to the erythemal response in the region above SPF 20. Then, we conducted the same experiment on all types of sunscreens by incorporating the photoaugmentative effect (FIG. 21). When the relationship with the reciprocity curve was observed, FIG. 21 showed a higher correlation than that shown in FIG. 22 where the photoaugmentative effect was not considered. It was thus made clear that especially in the region up to SPF 20 the photoaugmentative effect of UV-A does exist so that the reciprocity rule holds. We thus verified that UV-A has the photoaugmentative effect on the erythemal response.

Figure 23:
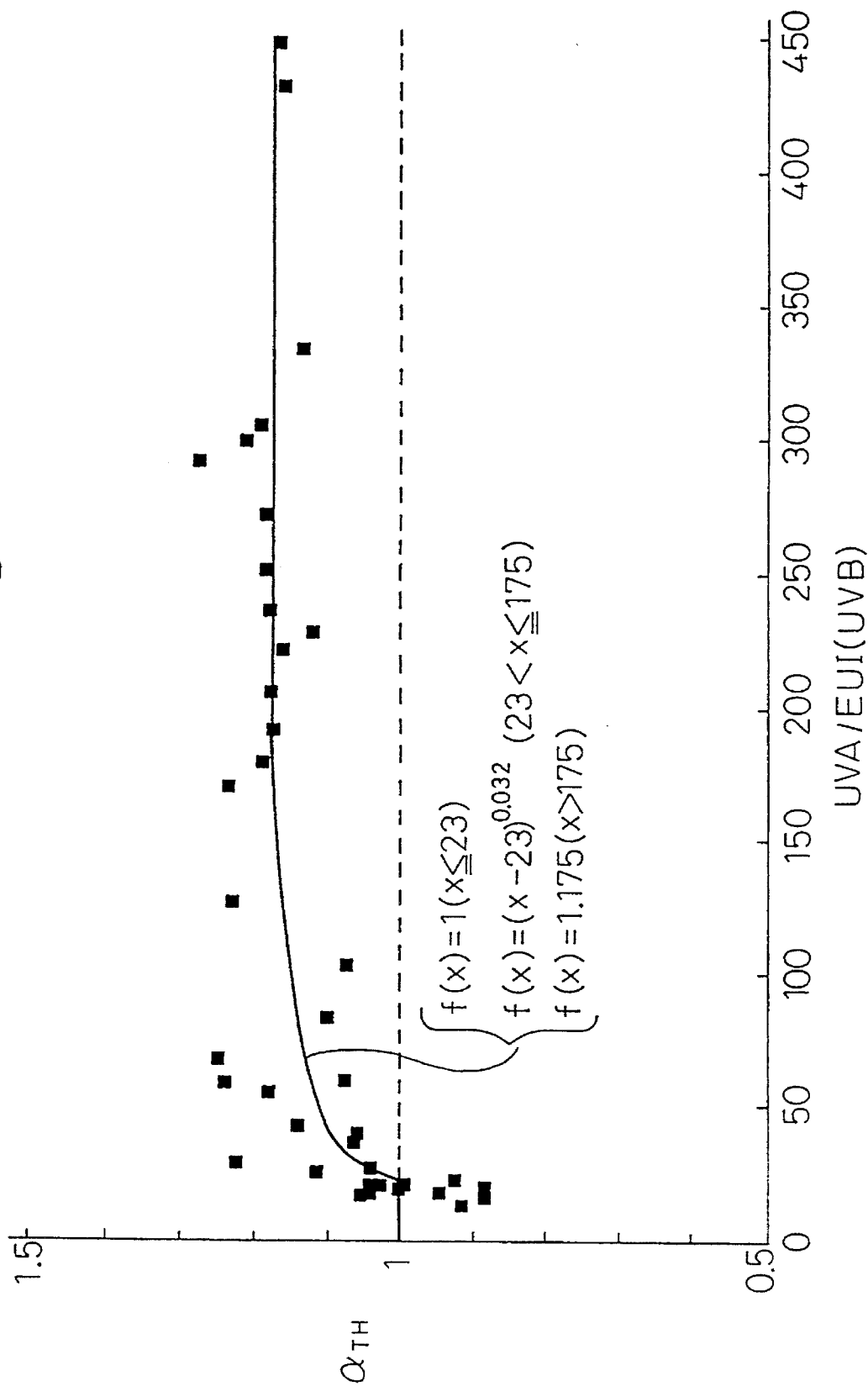
FIG. 23 is a diagram showing the relationship between UVA/EUI and $α_{TH}$.

We have so far discussed the evaluation of the UV-A photoaugmentative effect. On the other hand, this phenomenon may be recognized as the result of a synergistic effect between UV-A and UV-B, and it is possible to surmise that the ratio between UV-A and UV-B in the transmitted UV spectrum has some effect on this phenomenon. To verify this, the ratio between the transmitted UV-A intensity value and the EUI value ($\Sigma EE(\lambda)I(\lambda)$) in the 320 to 400 nm range is obtained first, and then, the theoretical value ($\alpha_{Th}$) of the base of the photoaugmentative effectiveness is calculated for each of the sunscreens with measured SPF 20 or less. The reason why the EUI value is used instead of using transmitted UV intensity is that the EUI value is nearly equal to the transmitted UV intensity. Each $\alpha_{Th}$ is calculated from the ratio between the theoretical value and actual measured value of the erythemal UV intensity, and the actual measured UV-A intensity, using equation (13). In FIG. 23, the theoretical value ($\alpha_{Th}$) of the base of the photoaugmentative effectiveness is plotted against the ratio of the transmitted UV-A intensity value to the EUI value ($\Sigma EE(\lambda)I(\lambda)$). As can be seen, the value of $\alpha$ increases with increasing proportion of the transmitted UV-A. This means that the photoaugmentative effect of UV-A is affected by the ratio of UV-A to UV-B. when the proportion of the biologically active UV-B is high, UV-B is the dominant cause of the erythemal response; conversely, when the proportion of UV-B is low, the photoaugmentative effect of UV-A is observed. From the relationship shown in FIG. 23, the following relations are determined.

$$\begin{aligned}\alpha_{TH} &= 1 \; (x \leq 23) \\ \alpha_{TH} &= (x - 23)^{0.032} \; (23 < x \leq 175) \\ \alpha_{TH} &= 1.175 \; (1.175 < x)\end{aligned} \quad (14)$$

where x=UV-A/EUI

Figure 24:
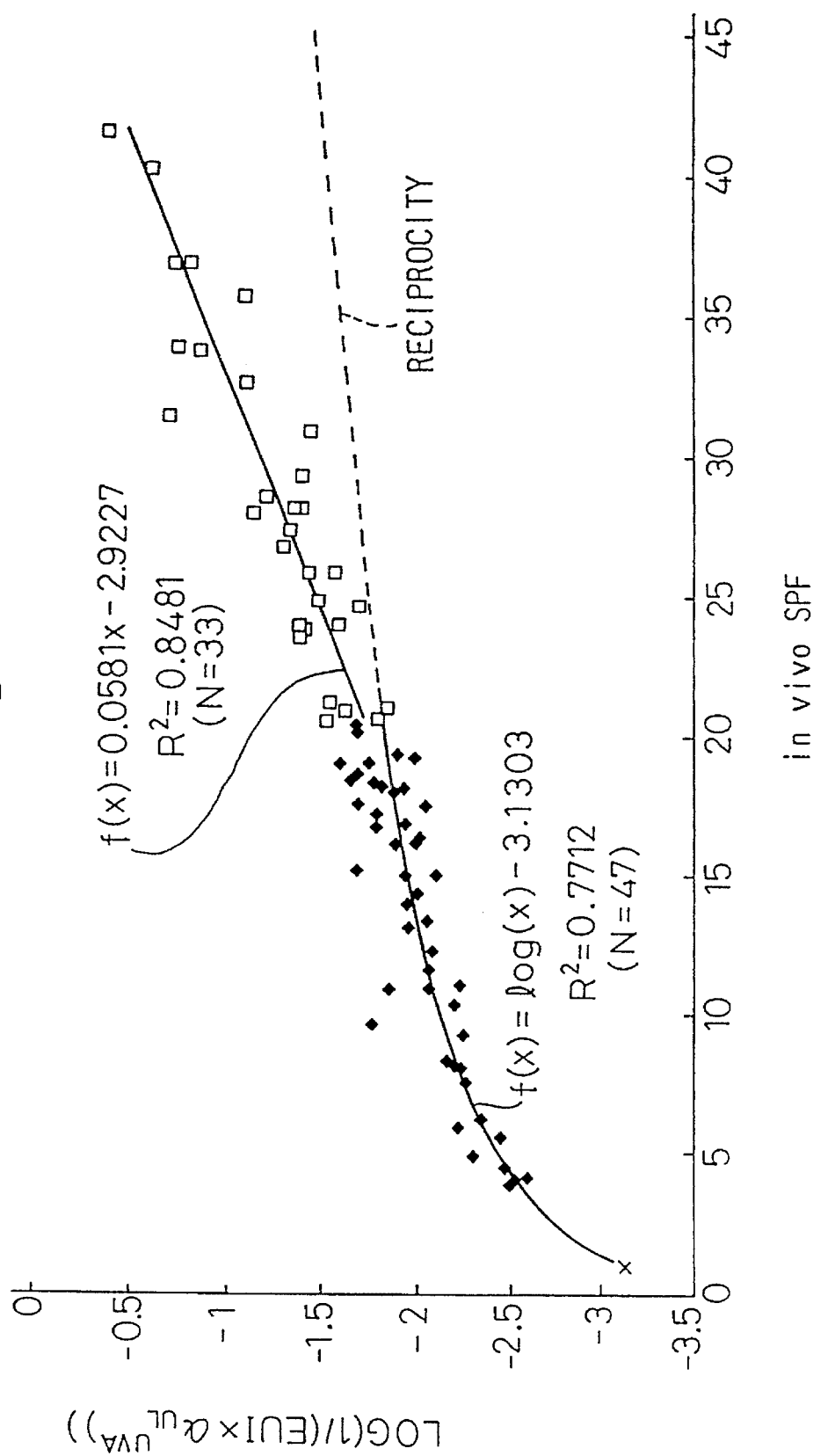
FIG. 24 is a diagram showing the relationship between $EUI_{UL}$ and in vivo SPF values for sunscreens of various material types.

Using equations (14) and (13), we calculated an ultimate theoretical EUI value ($EUI_{UL}$) incorporating the effect of the ratio UV-A/UV-B on the UVA photoaugmentative effect, to reevaluate the relationship with the SPF value of each of the sunscreens (FIG. 24). The results showed that for all the sunscreens the ultimate theoretical EUI values ($EUI_{UL}$) had high correlation with both the reciprocity curve and the SPF values. We were thus able to verify in a further clarified manner the presence of the UV-A photoaugmentative effect relating to the erythema response.

The curve where the reciprocity law holds is indicated by a dashed line in FIG. 24. As can be seen, the reciprocity law holds in the region of SPF 20 and below, but does non hold in the region of SPF above 20. More specifically, it was found that as far as the erythemal response of human skin is concerned, the reciprocity law, the basic principle of optical response, holds within a certain time, but does not hold outside that time. Instead, a possibility was suggested that there may exist a different rule having a biological effect. Accordingly, only calculation programs in which "reciprocity" and "non-reciprocity" are considered can predict the SPF value with high accuracy.

Figure 25:
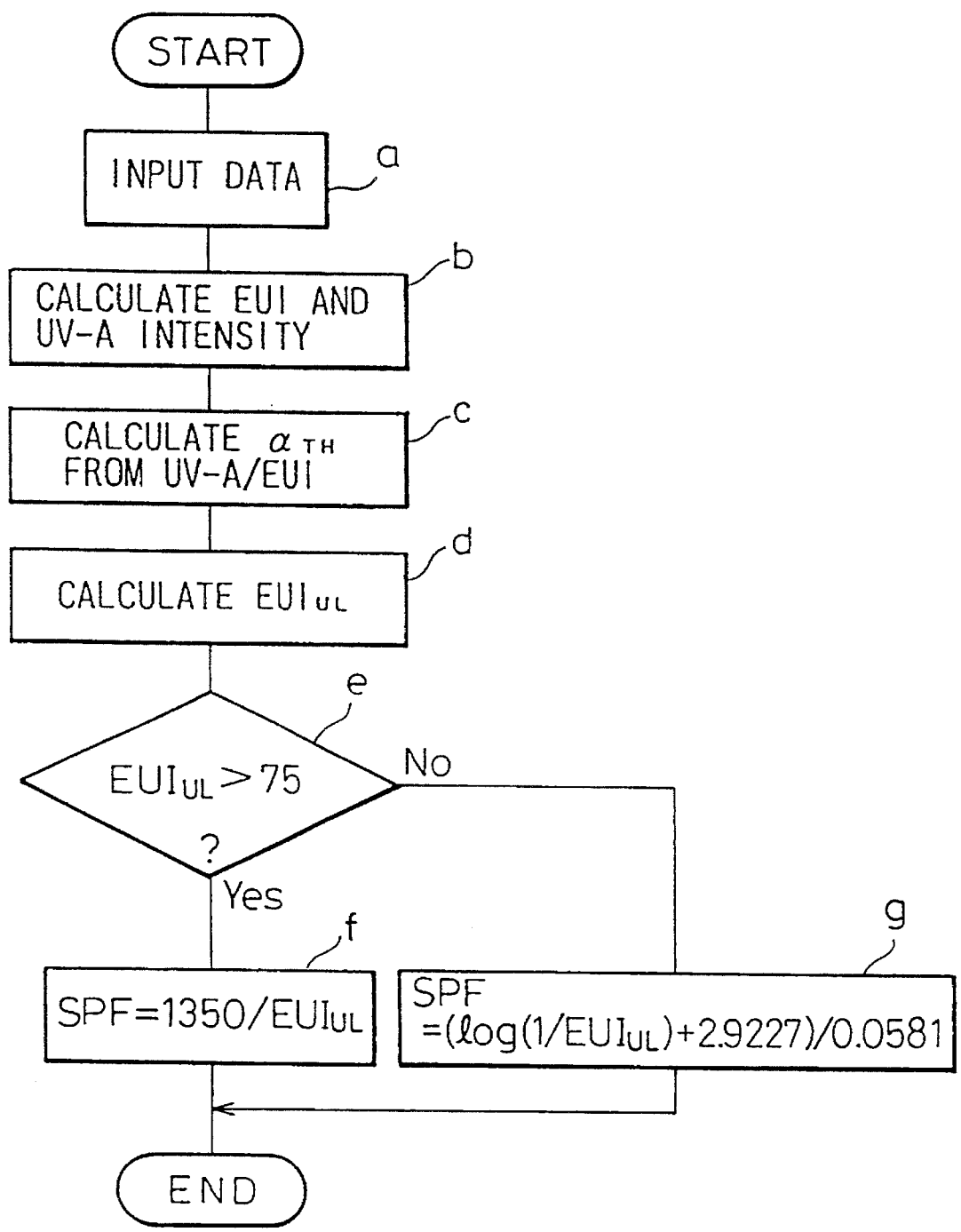
FIG. 25 is a flowchart illustrating an in vitro SPF measuring procedure according to a second embodiment of the invention.

FIG. 25 is a flowchart illustrating the processing performed by the personal computer 26 (FIG. 2) used in the SPF measuring apparatus according to the second embodiment of the invention. Measurement data $I(\lambda)$, taken on a sample with an application quantity of 2.0 mg/cm$^2$, is input from the detector 24 (step a) Then, using equation (9), EUI is calculated, and by summing $I(\lambda)$ from $\lambda=290$ to 400 nm, the UV-A intensity is calculated (step b). Using equation (14), $\alpha_{TH}$ is calculated from the value of UV-A/EUI (step c), and using equation $$EUI_{UL}=EUI\times\alpha_{TH}^{UVA}$$

the ultimate theoretical EUI value, $EUI_{UL}$, is calculated from the values of $\alpha_{TH}$, UV-A, and EUI (step d). Then, it is determined whether the value of $EUI_{UL}$ is larger than 75 (step e), and if $EUI_{UL}$ is larger than 75 (which corresponds to SPF<18), the SPF value is calculated using the following equation $$SPF=1350/EUI_{UL}$$

which is derived from equation (11) expressing the reciprocity rule (step f). IE $EUI_{UL}$ is not larger than 75, the SPF value is calculated using the following empirical equation (step g).

$$SPF=(log(1/EUI_{UL})+2.9227)/0.0581$$

FIG. 26 shows part of the measurement results. should be noted that the in vitro SPF values measured by the apparatus of the present invention are very close to in vivo SPF value, particularly in the higher SPF region.

We claim:

1. A method of measuring ultraviolet protection effectiveness of a sample, comprising the steps of:
   a) measuring the intensities of ultraviolet radiation at a plurality of wavelength sections of the ultraviolet radiation transmitted through the sample;
   b) calculating an erythema-inducing UV intensity by multiplying the intensities measured at said plurality of wavelength sections by erythemal effectiveness coefficients associated with the respective wavelength sections and by summing the resulting products;
   c) calculating a transmitted UV-A intensity by summing the intensities at the respective wavelength sections that lie within the wavelength range of UV-A;
   d) calculating a photoaugmentative effectiveness from said transmitted UV-A intensity;
   f) calculating an ultimate erythema-inducing UV intensity by multiplying said erythema-inducing UV intensity by said photoaugmentative effectiveness; and
   g) calculating an SPF value from said ultimate erythema-inducing UV intensity.

2. A method according to claim 1, wherein in step d), said photoaugmentative effectiveness is an exponential function of said transmitted UV-A intensity.

3. A method according to claim 2, wherein step a) includes
   applying said sample to a tape member transparent to ultraviolet radiation,
   irradiating said sample-applied tape member with ultraviolet radiation having a prescribed intensity distribution, and
   measuring the intensity of the ultraviolet radiation transmitted through said tape member.

4. A method according to claim 2, wherein the base of said exponential function is determined by the value of said erythema-inducing UV intensity.

5. A method according to claim 4, wherein step a) includes
   applying said sample to a tape member transparent to ultraviolet radiation,
   irradiating said sample-applied/tape member with ultraviolet radiation having a prescribed intensity distribution, and
   measuring the intensity of the ultraviolet radiation transmitted through said tape member.

6. A method according to claim 2, wherein the base of said exponential function is determined by the ratio of said transmitted UV-A intensity to said erythema-inducing UV intensity.

7. A method according to claim 6, wherein step a) includes
   applying said sample to a tape member transparent to ultraviolet radiation,
   irradiating said sample-applied tape member with ultraviolet radiation having a prescribed intensity distribution, and
   measuring the intensity of the ultraviolet radiation transmitted through said tape member.

8. A method according to claim 6, wherein in step g), when said ultimate erythema-inducing UV intensity is larger than a prescribed value, the SPF value is calculated by dividing a constant by said ultimate erythema-inducing UV intensity, and when said ultimate erythema-inducing UV intensity is not larger than the prescribed value, the SPF value is calculated in accordance with a prescribed empirical equation.

9. A method according to claim 8, wherein step a) includes
   applying said sample to a tape member transparent to ultraviolet radiation,
   irradiating said sample-applied tape member with ultraviolet radiation having a prescribed intensity distribution, and
   measuring the intensity of the ultraviolet radiation transmitted through said tape member.

10. A method according to claim 1, wherein step a) includes
    applying said sample to a tape member transparent to ultraviolet radiation,
    irradiating said sample-applied tape member with ultraviolet radiation having a prescribed intensity distribution, and
    measuring the intensity of the ultraviolet radiation transmitted through said tape member.

11. An apparatus for measuring ultraviolet protection effectiveness of a sample, comprising:
    means for measuring the intensities of ultraviolet radiation at a plurality of wavelength sections of the ultraviolet radiation transmitted through the sample;
    means for calculating an erythema-inducing UV intensity by multiplying the intensities measured at said plurality of wavelength sections by erythemal effectiveness coefficients associated with the respective wavelength sections and by summing the resulting products;
    means for calculating a transmitted UV-A intensity by summing the intensities at the respective wavelength sections that lie within the wavelength range of UV-A;

means for calculating a photoaugmentative effectiveness from said transmitted UV-A intensity;

means for calculating an ultimate erythema-inducing UV intensity by multiplying said erythema inducing UV intensity by said photoaugmentative effectiveness; and means for calculating an SPF value from said ultimate erythema-inducing UV intensity.

12. An apparatus according to claim 11, wherein said photoaugmentative effectiveness calculating means calculates said photoaugmentative effectiveness as an exponential function of said transmitted UV-A intensity.

13. An apparatus according to claim 12, wherein the base of said exponential function is determined by the value of said erythema-inducing UV intensity.

14. An apparatus according to claim 12, wherein the base of said exponential function is determined by the ratio of said transmitted UV-A intensity to said erythema-inducing UV intensity.

15. An apparatus according to claim 14, wherein when said ultimate erythema-inducing UV intensity is larger than a prescribed value, said SPF value calculating means calculates the SPF value by dividing a constant by said ultimate erythema-inducing UV intensity and, when said ultimate erythema-inducing UV intensity is not larger than the prescribed value, calculates the SPF value from said ultimate erythema-inducing UV intensity in accordance with a prescribed empirical equation.

* * * * *